United States Patent [19]
Brömme et al.

[11] Patent Number: 5,736,357
[45] Date of Patent: Apr. 7, 1998

[54] CATHESPIN O PROTEASE

[75] Inventors: Dieter Brömme, San Bruno; Kathleen Okamoto, Mountain View, both of Calif.

[73] Assignee: Arris Pharmaceutical, South San Francisco, Calif.

[21] Appl. No.: 330,121

[22] Filed: Oct. 27, 1994

[51] Int. Cl.$^6$ .............................. C12N 1/21; C12N 15/15; C12N 15/63; C12P 21/02
[52] U.S. Cl. .................... 435/69.1; 435/320.1; 435/325; 435/252.3; 435/254.11; 536/23.5
[58] Field of Search .................. 536/23.2; 435/219, 435/320.1, 240.2, 252.3, 325

[56] References Cited

U.S. PATENT DOCUMENTS 5,501,969  3/1996  Hastings et al. .................. 435/252.3

FOREIGN PATENT DOCUMENTS 9524182  9/1995  WIPO.

OTHER PUBLICATIONS

Drake, F. et al., "Identification of a Novel Osteoclast-Selective Human Cysteine Proteinase." *Journal of Bone and Mineral Research*, 9(Supp. 1):S177 (Abstract A110) (Aug. 1994).

Tezuka, K., et al., "Molecular Cloning of a Possible Cysteine Proteinase Predominantly Expressed in Osteoclasts", *The Journal of Biological Chemistry*, 269(2):1106–1109, (1994).

Delaisse, J.M., et al., "Inhibition of Bone Resorption in Culture by Inhibitors of Thiol Proteinases", *The Biochemical Society*, 192:365–368, (1980).

Delaisse, J.M., et al., "Collagenolytic Cysteine Proteinases of Bone Tissue", *The Biochemical Society*, 279:167–174, (1991).

Everts, V., et al., "Effects of the Proteinase Inhibitors Leupeptin and E–64 on Osteoclastic Bone Resorption", *Calcif Tissue Int.*, 43:172–178, (1988).

Sasaki, T., et al., "Cystein-Proteinase Localization in Osteoclasts: An Immunocytochemical Study", *Cell Tissue Res.*, 271:177–179, (1993).

Eeckhout Y., et al., "Possible Role and Mechanism of Action of Dissolved Calcium _ The Degradation of Bone Collagen by Lysosomal Cathepsins and Collagenase", *Biochem J.*, 272:529–532, (1990).

Van Noorden, C.J.F., et al., "Cysteine Proteinase Activity in Arthritic Rat Knee Joints and the Effects of a Selective Systemic Inhibitor. Z–Phe–AlaCH$_2$F", *The Journal of Rheumatology*, 15(10):1525–1535, (1988).

Delaisse, J.M., et al., "Mechanism of Mineral Solubilization and Matrix Degradation in Osteoclastic Bone Resorption", *Biology and Physiology of the Osteoclast*, Ch. 14:289–314, (1991).

Shi, G.P., et al., "Molecular Cloning of Human Cathepsin O, a Novel Endoproteinase and Homologue of Rabbit OC2", *FEBS Letters*, 357:129–134, (1995).

Inaoka, T., et al., "Molecular Cloning of Human cDNA for Cathepsin K: Novel Cysteine Proteinase Predominantly Expressed in Bone", *Biochem. Biophys. Res. Comm.*, 206(1):89–96 (1995).

Wiederanders et al., *J. Biol. Chem.* 267:13708–13713 (1992).

Tsukuba et al., *J. Biol. Chem.* 268:7276–7282 (1993).

*Primary Examiner*—Robert A. Wax
*Assistant Examiner*—Eric Grimes
*Attorney, Agent, or Firm*—Flehr Hohbach Test Albritton & Herbert, LLP; David J. Brezner; Robin M. Silva

[57] ABSTRACT

The invention relates to cathepsin O proteins, nucleic acids, and antibodies.

6 Claims, 10 Drawing Sheets

```
GCGCACTCAC AGTCGCAACC TTTCCCCTTC CTGACTTCCC GCTGACTTCC GCAATCCCGA      60
TGGAATAAAT CTAGCACCCC TGATGGTGTG CCCACACTTT GCTGCCGAAA CGAAGCCAGA     120
CAACAGATTT CCATCAGCAG C ATG TGG GGG CTC AAG GTT CTG CTG CTA CCT      171
                       Met Trp Gly Leu Lys Val Leu Leu Leu Pro
                        1                 5                 10

GTG GTG AGC TTT GCT CTG TAC CCT GAG GAG ATA CTG GAC ACC CAC TGG      219
Val Val Ser Phe Ala Leu Tyr Pro Glu Glu Ile Leu Asp Thr His Trp
             15                  20                  25

GAG CTA TGG AAG ACC CAC AGG AAG ACC CAC AGG AAG CAA TAT AAC AAC AAG GTG GAT      267
Glu Leu Trp Lys Thr His Arg Lys Gln Tyr Asn Asn Lys Val Asp
         30                  35                  40

GAA ATC TCT CGG CGT TTA ATT TGG GAA AAA AAC CTG AAG TAT ATT TCC      315
Glu Ile Ser Arg Arg Leu Ile Trp Glu Lys Asn Leu Lys Tyr Ile Ser
     45                  50                  55

ATC CAT AAC CTT GAG GCT TCT CTT GGT GTC CAT ACA TAT GAA CTG GCT      363
Ile His Asn Leu Glu Ala Ser Leu Gly Val His Thr Tyr Glu Leu Ala
 60                  65                  70

ATG AAC CAC CTG GGG GAC ATG ACC AGT GAA GAG GTG GTT CAG AAG ATG      411
Met Asn His Leu Gly Asp Met Thr Ser Glu Glu Val Val Gln Lys Met
 75                  80                  85                  90

ACT GGA CTC AAA GTA CCC CTG TCT CAT TCC CGC AGT AAT GAC ACC CTT      459
Thr Gly Leu Lys Val Pro Leu Ser His Ser Arg Ser Asn Asp Thr Leu
             95                 100                 105

TAT ATC CCA GAA GGT GAA TGG AGA GCC CCA GAC TCT GTC GAC TAT CGA      507
Tyr Ile Pro Glu Gly Glu Trp Arg Ala Pro Asp Ser Val Asp Tyr Arg
         110                 115                 120
```

FIG._1A

```
AAG AAA GGA TAT GTT ACT CCT GTC AAA AAT CAG GGT CAG TGT GGT TCC    555
Lys Lys Gly Tyr Val Thr Pro Val Lys Asn Gln Gly Gln Cys Gly Ser
125                     130                     135

TGT TGG GCT TTT AGC TCT GTG GGT GCC CTG GAG CAA GGC CTC AAG AAG    603
Cys Trp Ala Phe Ser Ser Val Gly Ala Leu Glu Gln Gly Leu Lys Lys
        140                     145                     150

AAA ACT GGC AAA CTC TTA AAT CTG AGT CCC CAG AAC CTA GTG GAT TGT    651
Lys Thr Gly Lys Leu Leu Asn Leu Ser Pro Gln Asn Leu Val Asp Cys
155                     160                     165                 170

GTG TCT GAG AAT GAT GGG GGG TGT GGA GGG GGC TAC ATG ACC AAT GCC TTC    699
Val Ser Glu Asn Asp Gly Gly Cys Gly Gly Gly Tyr Met Thr Asn Ala Phe
            175                     180                     185

CAA TAT GTG CAG AAG AAC CGG GGT ATT GAC TCT GAA GAT GCC TAC CCA    747
Gln Tyr Val Gln Lys Asn Arg Gly Ile Asp Ser Glu Asp Ala Tyr Pro
        190                     195                     200

TAT GTG GGA CAG GAA GAG AGT TGT ATG TAC AAC CCA ACA GGC AAG GCA    795
Tyr Val Gly Gln Glu Glu Ser Cys Met Tyr Asn Pro Thr Gly Lys Ala
    205                     210                     215

GCT AAA TGC AGA GGG TAC AGA GAG ATC CCC GAG GGG AAT GAG AAA GCC    843
Ala Lys Cys Arg Gly Tyr Arg Glu Ile Pro Glu Gly Asn Glu Lys Ala
220                     225                     230

CTG AAG AGG GCA GTG GCC CGA GTG GGA CCT GTC TCT GTG GCC ATT GAT    891
Leu Lys Arg Ala Val Ala Arg Val Gly Pro Val Ser Val Ala Ile Asp
235                     240                     245                 250

GCA AGC CTG ACC TCC TTC CAG TTT TAC AGC AAA GGT GTG TAT TAT GAT    939
Ala Ser Leu Thr Ser Phe Gln Phe Tyr Ser Lys Gly Val Tyr Tyr Asp
        255                     260                     265
```

FIG._1B

```
GAA AGC TGC AAT AGC GAT AAT CTG AAC CAT GCG GTT TTG GCA GTG GGA    987
Glu Ser Cys Asn Ser Asp Asn Leu Asn His Ala Val Leu Ala Val Gly
                270                 275                 280

TAT GGA ATC CAG AAG GGA AAC AAG CAC TGG ATA ATT AAA AAC AGC TGG   1035
Tyr Gly Ile Gln Lys Gly Asn Lys His Trp Ile Ile Lys Asn Ser Trp
            285                 290                 295

GGA GAA AAC TGG GGA AAC AAA GGA TAT ATC CTC ATG GCT CGA AAT AAG   1083
Gly Glu Asn Trp Gly Asn Lys Gly Tyr Ile Leu Met Ala Arg Asn Lys
        300                 305                 310

AAC AAC GCC TGT GGC ATT GCC AAC CTG GCC AGC TTC CCC AAG ATG       1128
Asn Asn Ala Cys Gly Ile Ala Asn Leu Ala Ser Phe Pro Lys Met
    315                 320                 325

TGACTCCAGC CAGCCAAATC CATCCTGCTC TTCCATTTCT TCCACGATGG TGCAGTGTAA  1188

CGATGCACTT TGGAAGGGAG TTGGTGTGCT ATTTTTGAAG CAGATGTGGT GATACTGAGA  1248

TTGTCTGTTC AGTTTCCCCA TTTGTTTGTG CTTCAAATGA TCCTTCCTAC TTTGCTTCTC  1308

TCCACCCATG ACCTTTTTCA CTGTGGCCAT CAGGACTTTC CCTGACAGCT GTGTACTCTT  1368

AGGCTAAGAG ATGTGACTAC AGCCTGCCCC TGACTGTGTT GTCCCAGGGC TGATGCTGTA  1428

CAGGTACAGG CTGGAGATTT TCACATAGGT TAGATTCTCA TTCACGGGAC CCGG        1482
```

*FIG._1C*

```
HCat0   MWGLKVLL-- ---L--PVVS FA-LYPEEIL DTHWEL-WKK TH-RKQYNNK VDEISRRL    48
OC2     MWGLKVLL-- ---L--PVVS FA-LHPEEIL DTQWEL-WKK TY-SKQYNSK VDEISRRL    48
HCatS   MKRLVCVL-- ---LVC-SSA VAQLHKDPTL DHHWHL-WKK TY-GKQYKEK NEEAVRRL    50
HCatL   MNPTLILA-- ---AFCLGIA SATLTFDHSL EAQWTK-WKA MHNRL-YGM- NEEGWRRA    50
HCatH   MWATLPLLCA GAWLLCVPVC GAAELCVNSL EKFHFKSWMS KHRKT-YST- -EEYHHRL    55
HCatB   MWQLWASLC- -----CLLVL ANA------- ---------- -RSRPSFHPV S-DEL-VN    31
cons.   M......l.. ......l... .a........ .......w.. ..........  .E...r.

HCat0   -IWEKNLKYI SIHNLEASLG VHTYLLAMNH LGDMTSEEVV QRMTGLKVPL SHSRSND     104
OC2     -IWEKNLKHI SIHNLEASLG VHTYELAMNH LGDMTSEEVV QRMTGLKVPP SRSHSND     104
HCatS   -IWEKNLKFV MLHNLEHSMG MHSYDLGMNH LGDMTSEEVM SLMSSLRVP- -SQWQRN     104
HCatL   -VWEKNMKMI ELHNQEYREG KHSFTMAMNA FGDMTSEEFR QVMNGFQ--- NRKPRKG     103
HCatH   QTFASNWRKI NAHN----NG NHTFKMALNQ FSDMSFAEIK HKY-LWSEPQ NCSATK-     106
HCatB   YVNKRNTTWQ AGHNFYNVDM SYLKRLCGTF LGGPKPPQRV MFTEDLK--- -------      79
cons.   ......N... .HN.......g .h........ .n........ .m....e...  .....p.

HCat0   TLYIPEWEGR APDSVDYRKK G----YVTPV KNQGQCGSCW AFSSVGALEG QLKKKTG    157
OC2     TLYIPDWEGR TPDSIDYRKK G----YVTPV KNQGQCGSCW AFSSVGALEG QLKKKTG    157
HCatS   ITYKSNPNRI LPDSVDWREK G----CVTEV KYQGSCGACW AFSAVGALEA QLKLKTG    157
HCatL   KVFQEPLFYE APRSVDWREK G----YVTPV KNQGQCGSCW AFSATGALEG QMFRKTG    156
HCatH   SNYLRG-TGP YPPSVDWRKK GN---FVSPV KNQGACGSCW TFSTTGALES AIAIATG    159
HCatB   LPASFDAREQ WPQCPTIKEI RDQGSCGSCW AFGAVEAISD RICIHTN           126
cons.   ..........  .P.S.DwRek .....v..v  k.QG.CGsCW aFs..gAle. .......g

*
HCat0   KLLNL--SPQ NLVDCVSE-- -NDGCGGGYM TNAFQYVQKN RGIDSEDAY- -----P    202
OC2     KLLNL--SPQ NLVDCVSE-- -NYGCGGGYM TNAFQYVQRN RGIDSEDAY- -----P    202
HCatS   KLVSL--SAQ NLVDCSTEKY GNKGCNGGFM TTAFQYIIDN KGIDSDASY- -----P    205
HCatL   RLISL--SEQ NLVDCSGPQ- GNEGCNGGLM DYAFQYVQDN GGLDSEESY- -----P    203
HCatH   KMLSL--AEQ QLVDCA-QDF NNYGCQGGLP SQAFEYILYN KGIMGEDTY- -----P    206
HCatB   AHVSVEVSAE DLLTCCGSMC GD-GCNGGYP AEAWNF-WTR KGLVSGGLYE SHVGCRP    181
cons.   ....l..s.q  .LvdC..... .n.GC.GG.. .A..y....n  .G..s..Y. ......P
```

FIG._2A

```
HCat0   Y------------- -------------V GQEESCM---  ---YNPTGKA AKCRGYREIP EGN-EKA  234
OC2     Y------------- -------------V GQDESCM---  ---YNPTGKA AKCRGYREIP EGN-EKA  234
HCatS   Y-------------  -------------K AMDQKCQ---  ---YDSKYRA ATCSKYTELP YGR-EDV  237
HCatL   Y-------------  -------------E ATEESCK---  ---YNPKYSV ANDTGFVDIP K-Q-EKA  234
HCatH   Y-------------  -------------Q GKDGYCK---  ---FQPGKAI GFVKDVANIT IYD-EEA  239
HCatB   YSIPPCEHHV NGSRPPCTGE GDTPKCSKIC EPGYSPTYKQ DKHYGYNSYS VSNSEKD  238
cons.   Y.........  .........  ......C...  ......y.p.  .........  ...E..

HCat0   LKRAVARVGP VSVAIDASLT SFQFYSKGVY YDESC--NSD NLN-HAVLAV GYG----   284
OC2     LKRAVARVGP VSVAIDASLT SFQFYSKGVY YDENC--SSD NVN-HAVLAV GYG----   284
HCatS   LKEAVANKGP VSVGVDARHP SFFLYRSGVY Y-EPS--CTQ NVN-HGVLVV GYG----   286
HCatL   LMKAVATVGP ISVAIDAGHE SFLFYKEGIY FEPDC--SSE DMD-HGVLVV GYGFEST   288
HCatH   MVEAVALYNP VSFAFEVTQD -FMMYRTGIY SSTSCHKTPD KVN-HAVLAV GYG----   289
HCatB   IMAEIYKNGP VEGAFSV-YS DFLLYKSGVY Q-----HVTGE MMGGHAIRIL GWGVE--   288
cons.   ...ava..gP vs.a...... .F..Y..G.Y ..........  ....H.vl.v GyG....

HCat0   IQKGNKHWII KNSWGENWGN KGYILMARNK NNACGIANLA SF--PK---M   329
OC2     IQKGNKHWII KNSWGESWGN KGYILMARNK NNACGIANLA SF--PK---M   329
HCatS   DLNGKEYWLV KNSWGHNFGE EGYIRMARNK GNHCGIASFP SY--PE---I   331
HCatL   ESDNNKYWLV KNSWGEEWGM GGYVKMAKDR RNHCGIASAA SY--PT---V   333
HCatH   EKNGIPYWIV KNSWGPQWGM NGYFLIERGK -NMCGLAACA SYPIPL---V   335
HCatB   --NGTPYWLV ANSWNTDWGD NGFFKILGGQ -DHCGIESEV VAGIPRTDQY WEKI   339
cons.   ...g...W.. kNSWg..wG. .Gy....... .n.CGia... ....P.....
```

*FIG._2B*

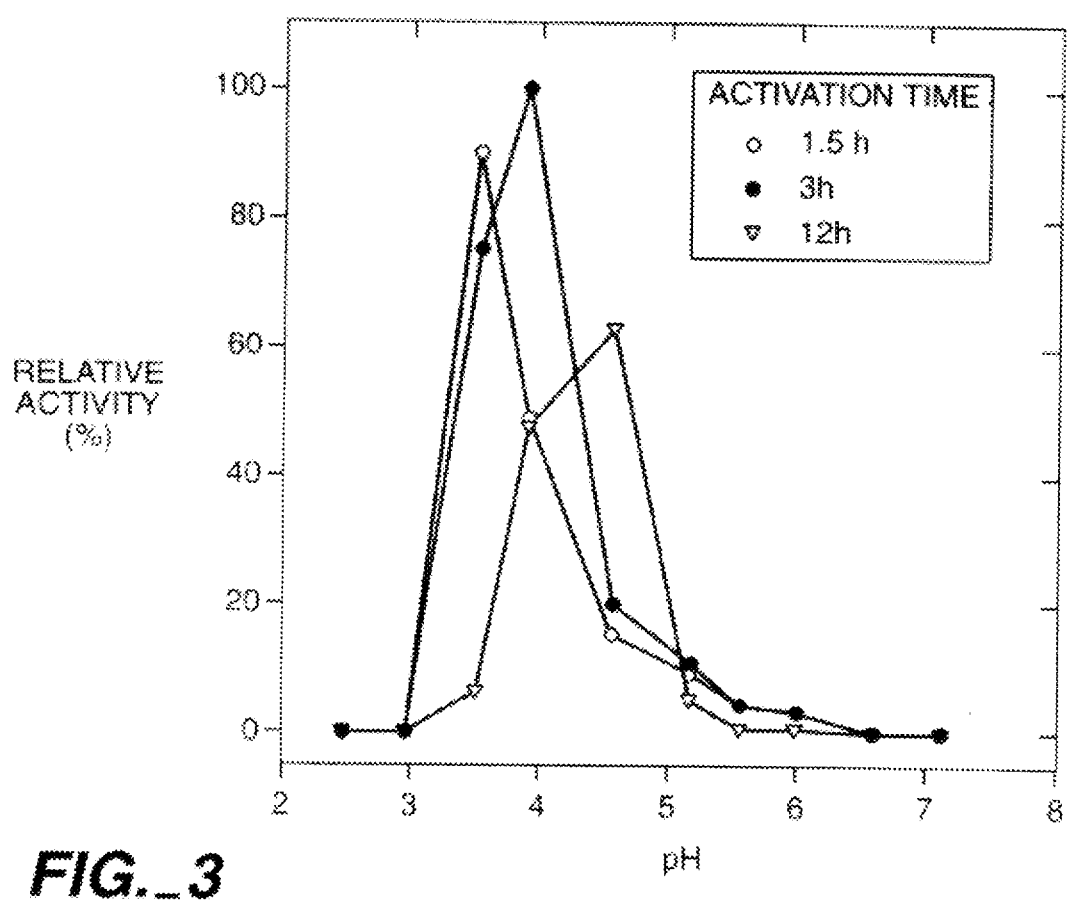
FIG._3
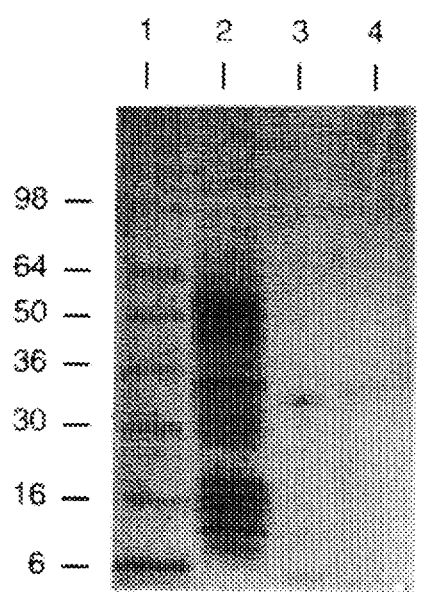
FIG._4

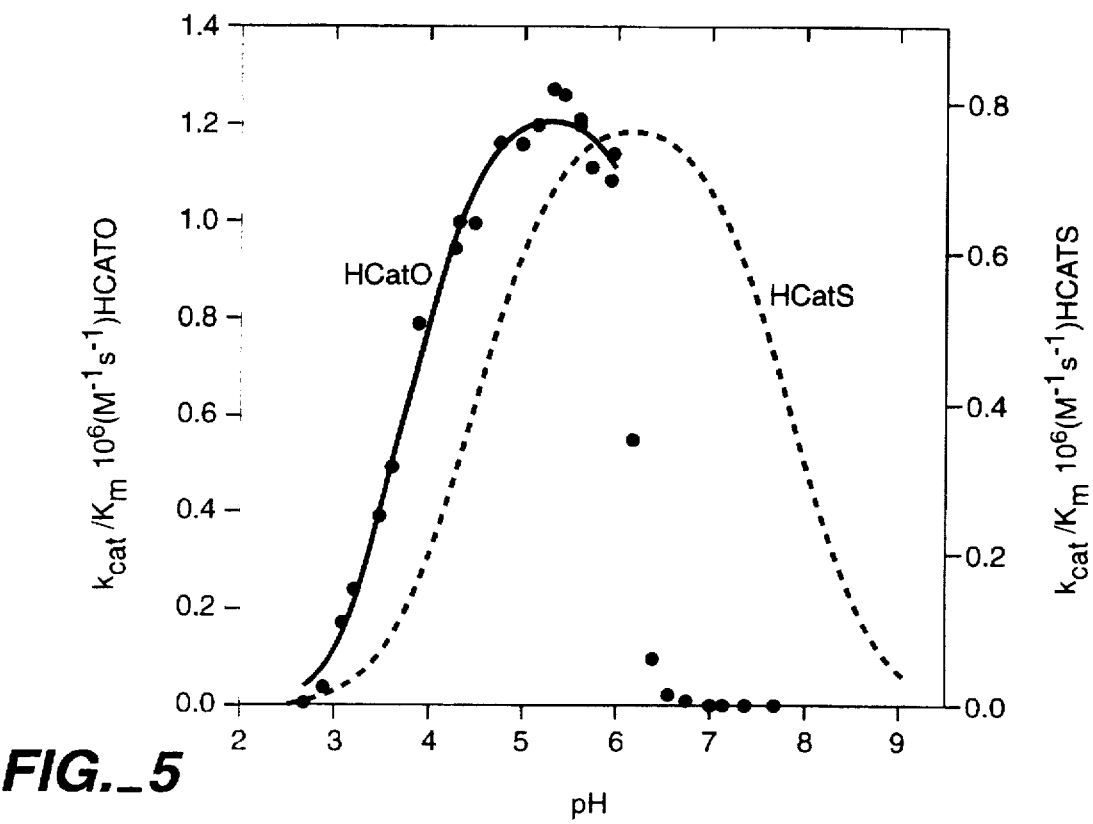
FIG._5
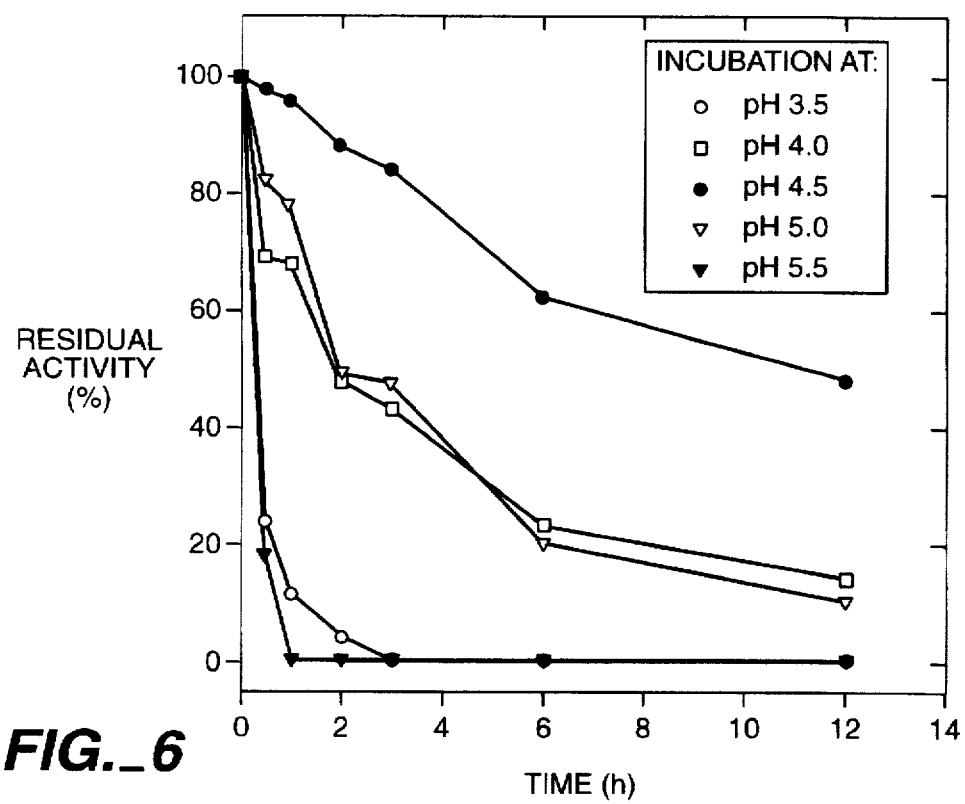
FIG._6

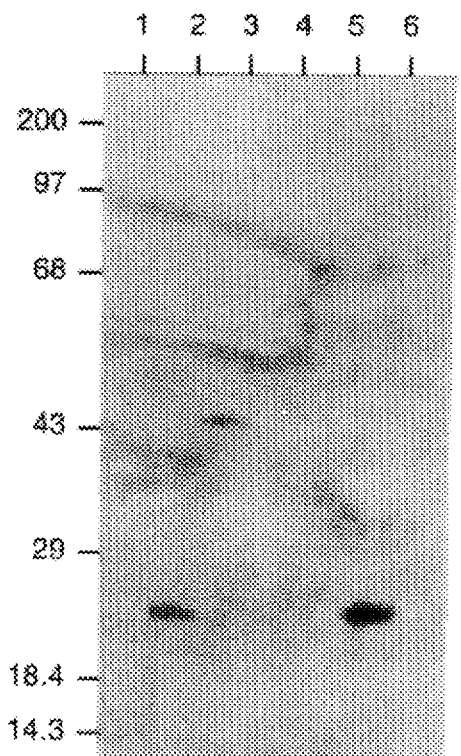
FIG._7
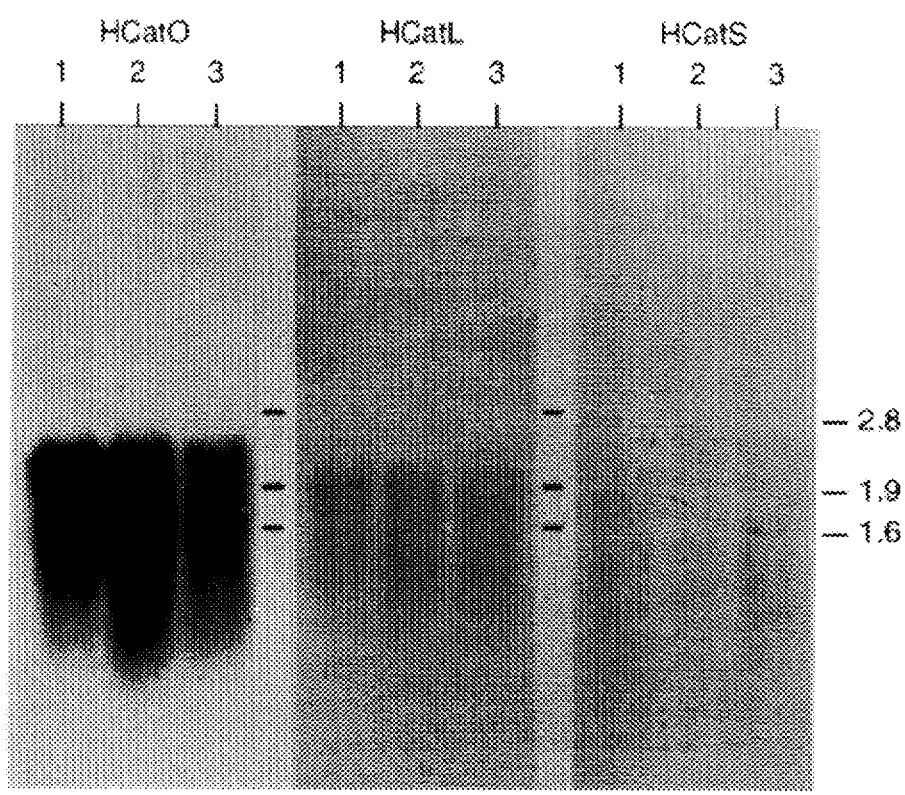
FIG._8

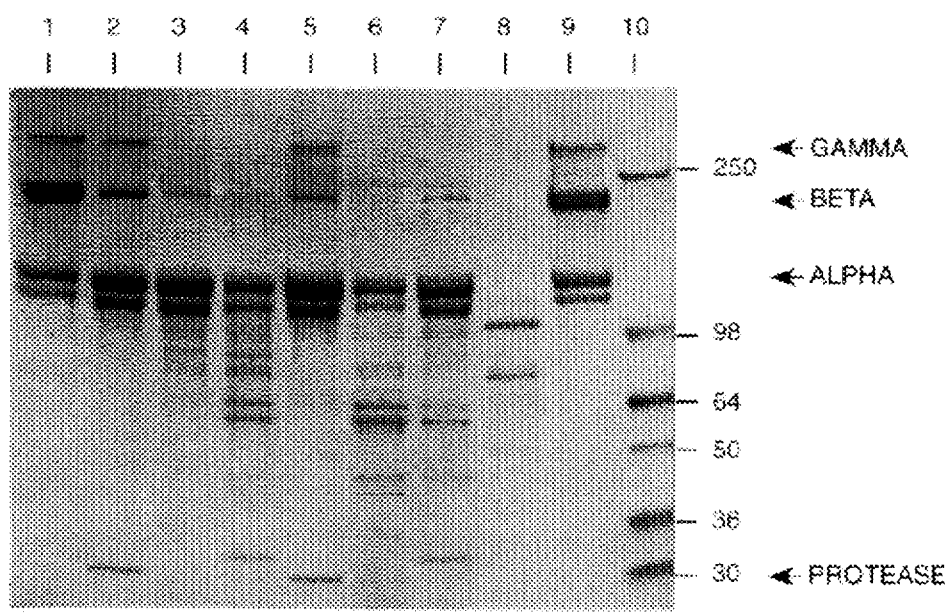
FIG._9

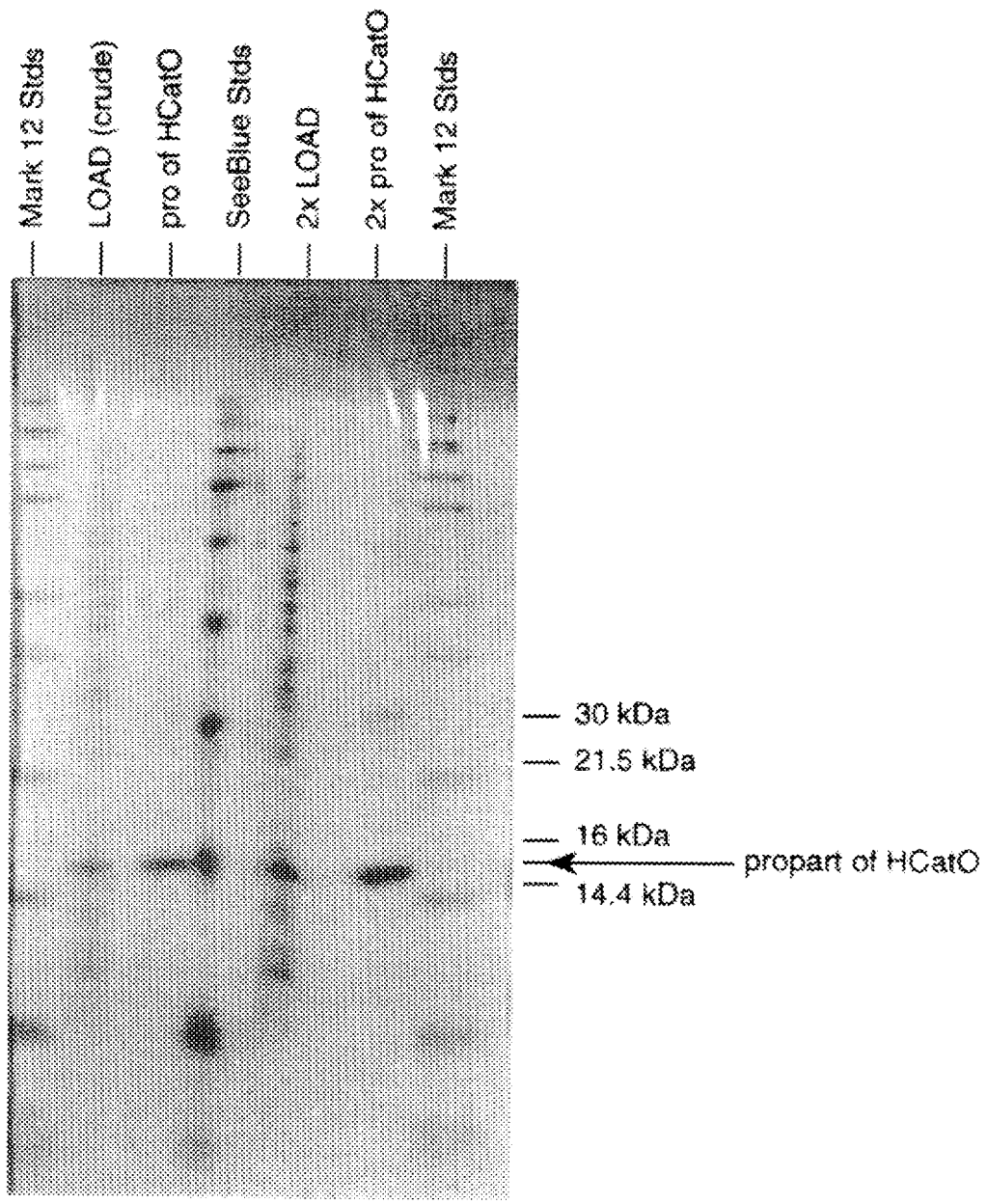
FIG._10

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1482 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 142..1128

( x i ) SEQUENCE DESCRIPTION: SEQ ID NO:1:

```
GCGCACTCAC AGTCGCAACC TTTCCCCTTC CTGACTTCCC GCTGACTTCC GCAATCCCGA         60

TGGAATAAAT CTAGCACCCC TGATGGTGTG CCCACACTTT GCTGCCGAAA CGAAGCCAGA        120

CAACAGATTT CCATCAGCAG C ATG TGG GGG CTC AAG GTT CTG CTG CTA CCT         171
                        Met Trp Gly Leu Lys Val Leu Leu Leu Pro
                         1                5                  10

GTG GTG AGC TTT GCT CTG TAC CCT GAG GAG ATA CTG GAC ACC CAC TGG         219
Val Val Ser Phe Ala Leu Tyr Pro Glu Glu Ile Leu Asp Thr His Trp
             15                  20                  25

GAG CTA TGG AAG AAG ACC CAC AGG AAG CAA TAT AAC AAC AAG GTG GAT         267
Glu Leu Trp Lys Lys Thr His Arg Lys Gln Tyr Asn Asn Lys Val Asp
         30                  35                  40

GAA ATC TCT CGG CGT TTA ATT TGG GAA AAA AAC CTG AAG TAT ATT TCC         315
Glu Ile Ser Arg Arg Leu Ile Trp Glu Lys Asn Leu Lys Tyr Ile Ser
     45                  50                  55

ATC CAT AAC CTT GAG GCT TCT CTT GGT GTC CAT ACA TAT GAA CTG GCT         363
Ile His Asn Leu Glu Ala Ser Leu Gly Val His Thr Tyr Glu Leu Ala
 60                  65                  70

ATG AAC CAC CTG GGG GAC ATG ACC AGT GAA GAG GTG GTT CAG AAG ATG         411
Met Asn His Leu Gly Asp Met Thr Ser Glu Glu Val Val Gln Lys Met
 75                  80                  85                  90

ACT GGA CTC AAA GTA CCC CTG TCT CAT TCC CGC AGT AAT GAC ACC CTT         459
Thr Gly Leu Lys Val Pro Leu Ser His Ser Arg Ser Asn Asp Thr Leu
                 95                 100                 105

TAT ATC CCA GAA TGG GAA GGT AGA GCC CCA GAC TCT GTC GAC TAT CGA         507
Tyr Ile Pro Glu Trp Glu Gly Arg Ala Pro Asp Ser Val Asp Tyr Arg
             110                 115                 120

AAG AAA GGA TAT GTT ACT CCT GTC AAA AAT CAG GGT CAG TGT GGT TCC         555
Lys Lys Gly Tyr Val Thr Pro Val Lys Asn Gln Gly Gln Cys Gly Ser
```

|  |  |  |  |  |  |  |  |  |  |  |  |  |  |  |  |
|--|--|--|--|--|--|--|--|--|--|--|--|--|--|--|--|
|  | 125 |  |  |  | 130 |  |  |  |  | 135 |  |  |  |  |  |
| TGT | TGG | GCT | TTT | AGC | TCT | GTG | GGT | GCC | CTG | GAG | GGC | CAA | CTC | AAG | AAG | 603 |
| Cys | Trp | Ala | Phe | Ser | Ser | Val | Gly | Ala | Leu | Glu | Gly | Gln | Leu | Lys | Lys |
|  | 140 |  |  |  | 145 |  |  |  |  | 150 |  |  |  |  |  |
| AAA | ACT | GGC | AAA | CTC | TTA | AAT | CTG | AGT | CCC | CAG | AAC | CTA | GTG | GAT | TGT | 651 |
| Lys | Thr | Gly | Lys | Leu | Leu | Asn | Leu | Ser | Pro | Gln | Asn | Leu | Val | Asp | Cys |
| 155 |  |  |  |  | 160 |  |  |  |  | 165 |  |  |  |  | 170 |
| GTG | TCT | GAG | AAT | GAT | GGC | TGT | GGA | GGG | GGC | TAC | ATG | ACC | AAT | GCC | TTC | 699 |
| Val | Ser | Glu | Asn | Asp | Gly | Cys | Gly | Gly | Gly | Tyr | Met | Thr | Asn | Ala | Phe |
|  |  |  |  | 175 |  |  |  |  | 180 |  |  |  |  | 185 |  |
| CAA | TAT | GTG | CAG | AAG | AAC | CGG | GGT | ATT | GAC | TCT | GAA | GAT | GCC | TAC | CCA | 747 |
| Gln | Tyr | Val | Gln | Lys | Asn | Arg | Gly | Ile | Asp | Ser | Glu | Asp | Ala | Tyr | Pro |
|  |  |  | 190 |  |  |  |  | 195 |  |  |  |  | 200 |  |  |
| TAT | GTG | GGA | CAG | GAA | GAG | AGT | TGT | ATG | TAC | AAC | CCA | ACA | GGC | AAG | GCA | 795 |
| Tyr | Val | Gly | Gln | Glu | Glu | Ser | Cys | Met | Tyr | Asn | Pro | Thr | Gly | Lys | Ala |
|  |  | 205 |  |  |  |  | 210 |  |  |  |  | 215 |  |  |  |
| GCT | AAA | TGC | AGA | GGG | TAC | AGA | GAG | ATC | CCC | GAG | GGG | AAT | GAG | AAA | GCC | 843 |
| Ala | Lys | Cys | Arg | Gly | Tyr | Arg | Glu | Ile | Pro | Glu | Gly | Asn | Glu | Lys | Ala |
|  | 220 |  |  |  |  | 225 |  |  |  |  | 230 |  |  |  |  |
| CTG | AAG | AGG | GCA | GTG | GCC | CGA | GTG | GGA | CCT | GTC | TCT | GTG | GCC | ATT | GAT | 891 |
| Leu | Lys | Arg | Ala | Val | Ala | Arg | Val | Gly | Pro | Val | Ser | Val | Ala | Ile | Asp |
| 235 |  |  |  |  | 240 |  |  |  |  | 245 |  |  |  |  | 250 |
| GCA | AGC | CTG | ACC | TCC | TTC | CAG | TTT | TAC | AGC | AAA | GGT | GTG | TAT | TAT | GAT | 939 |
| Ala | Ser | Leu | Thr | Ser | Phe | Gln | Phe | Tyr | Ser | Lys | Gly | Val | Tyr | Tyr | Asp |
|  |  |  |  | 255 |  |  |  |  | 260 |  |  |  |  | 265 |  |
| GAA | AGC | TGC | AAT | AGC | GAT | AAT | CTG | AAC | CAT | GCG | GTT | TTG | GCA | GTG | GGA | 987 |
| Glu | Ser | Cys | Asn | Ser | Asp | Asn | Leu | Asn | His | Ala | Val | Leu | Ala | Val | Gly |
|  |  | 270 |  |  |  |  | 275 |  |  |  |  | 280 |  |  |  |
| TAT | GGA | ATC | CAG | AAG | GGA | AAC | AAG | CAC | TGG | ATA | ATT | AAA | AAC | AGC | TGG | 1035 |
| Tyr | Gly | Ile | Gln | Lys | Gly | Asn | Lys | His | Trp | Ile | Ile | Lys | Asn | Ser | Trp |
|  |  | 285 |  |  |  |  | 290 |  |  |  |  | 295 |  |  |  |
| GGA | GAA | AAC | TGG | GGA | AAC | AAA | GGA | TAT | ATC | CTC | ATG | GCT | CGA | AAT | AAG | 1083 |
| Gly | Glu | Asn | Trp | Gly | Asn | Lys | Gly | Tyr | Ile | Leu | Met | Ala | Arg | Asn | Lys |
|  | 300 |  |  |  |  | 305 |  |  |  |  | 310 |  |  |  |  |
| AAC | AAC | GCC | TGT | GGC | ATT | GCC | AAC | CTG | GCC | AGC | TTC | CCC | AAG | ATG |  | 1128 |
| Asn | Asn | Ala | Cys | Gly | Ile | Ala | Asn | Leu | Ala | Ser | Phe | Pro | Lys | Met |
| 315 |  |  |  |  | 320 |  |  |  |  | 325 |  |  |  |  |

TGACTCCAGC CAGCCAAATC CATCCTGCTC TTCCATTTCT TCCACGATGG TGCAGTGTAA 1188

CGATGCACTT TGGAAGGGAG TTGGTGTGCT ATTTTTGAAG CAGATGTGGT GATACTGAGA 1248

TTGTCTGTTC AGTTTCCCCA TTTGTTGTG CTTCAAATGA TCCTTCCTAC TTTGCTTCTC 1308

TCCACCCATG ACCTTTTTCA CTGTGGCCAT CAGGACTTTC CCTGACAGCT GTGTACTCTT 1368

AGGCTAAGAG ATGTGACTAC AGCCTGCCCC TGACTGTGTT GTCCCAGGGC TGATGCTGTA 1428

CAGGTACAGG CTGGAGATTT TCACATAGGT TAGATTCTCA TTCACGGGAC CCGG 1482

( 2 ) INFORMATION FOR SEQ ID NO:2:

( i ) SEQUENCE CHARACTERISTICS:
        ( A ) LENGTH: 329 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Trp | Gly | Leu | Lys | Val | Leu | Leu | Pro | Val | Val | Ser | Phe | Ala | Leu |
|--|--|--|--|--|--|--|--|--|--|--|--|--|--|--|
| 1 |  |  |  | 5 |  |  |  |  | 10 |  |  |  |  | 15 |
| Tyr | Pro | Glu | Glu | Ile | Leu | Asp | Thr | His | Trp | Glu | Leu | Trp | Lys | Lys | Thr |
|  |  |  | 20 |  |  |  |  | 25 |  |  |  |  | 30 |  |  |

His Arg Lys Gln Tyr Asn Asn Lys Val Asp Glu Ile Ser Arg Arg Leu
         35                  40                  45

Ile Trp Glu Lys Asn Leu Lys Tyr Ile Ser Ile His Asn Leu Glu Ala
     50                  55                  60

Ser Leu Gly Val His Thr Tyr Glu Leu Ala Met Asn His Leu Gly Asp
 65                  70                  75                  80

Met Thr Ser Glu Glu Val Val Gln Lys Met Thr Gly Leu Lys Val Pro
                 85                  90                  95

Leu Ser His Ser Arg Ser Asn Asp Thr Leu Tyr Ile Pro Glu Trp Glu
             100                 105                 110

Gly Arg Ala Pro Asp Ser Val Asp Tyr Arg Lys Lys Gly Tyr Val Thr
         115                 120                 125

Pro Val Lys Asn Gln Gly Gln Cys Gly Ser Cys Trp Ala Phe Ser Ser
 130                 135                 140

Val Gly Ala Leu Glu Gly Gln Leu Lys Lys Lys Thr Gly Lys Leu Leu
145                 150                 155                 160

Asn Leu Ser Pro Gln Asn Leu Val Asp Cys Val Ser Glu Asn Asp Gly
             165                 170                 175

Cys Gly Gly Gly Tyr Met Thr Asn Ala Phe Gln Tyr Val Gln Lys Asn
         180                 185                 190

Arg Gly Ile Asp Ser Glu Asp Ala Tyr Pro Tyr Val Gly Gln Glu Glu
         195                 200                 205

Ser Cys Met Tyr Asn Pro Thr Gly Lys Ala Ala Lys Cys Arg Gly Tyr
 210                 215                 220

Arg Glu Ile Pro Glu Gly Asn Glu Lys Ala Leu Lys Arg Ala Val Ala
225                 230                 235                 240

Arg Val Gly Pro Val Ser Val Ala Ile Asp Ala Ser Leu Thr Ser Phe
                 245                 250                 255

Gln Phe Tyr Ser Lys Gly Val Tyr Tyr Asp Glu Ser Cys Asn Ser Asp
             260                 265                 270

Asn Leu Asn His Ala Val Leu Ala Val Gly Tyr Gly Ile Gln Lys Gly
         275                 280                 285

Asn Lys His Trp Ile Ile Lys Asn Ser Trp Gly Glu Asn Trp Gly Asn
     290                 295                 300

Lys Gly Tyr Ile Leu Met Ala Arg Asn Lys Asn Asn Ala Cys Gly Ile
305                 310                 315                 320

Ala Asn Leu Ala Ser Phe Pro Lys Met
                 325

( 2 ) INFORMATION FOR SEQ ID NO:3:

( i ) SEQUENCE CHARACTERISTICS:
        ( A ) LENGTH: 329 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:3:

Met Trp Gly Leu Lys Val Leu Leu Leu Pro Val Val Ser Phe Ala Leu
 1                   5                  10                  15

His Pro Glu Glu Ile Leu Asp Thr Gln Trp Glu Leu Trp Lys Lys Thr
                 20                  25                  30

Tyr Ser Lys Gln Tyr Asn Ser Lys Val Asp Glu Ile Ser Arg Arg Leu
             35                  40                  45

Ile Trp Glu Lys Asn Leu Lys His Ile Ser Ile His Asn Leu Glu Ala

|     |     |     |     |     |     |     |     |     |     |     |     |     |     |     |     |
|---|---|---|---|---|---|---|---|---|---|---|---|---|---|---|---|
|     |     |     |     | 50  |     |     |     |     | 55  |     |     |     |     | 60  |     |
| Ser | Leu | Gly | Val | His | Thr | Tyr | Glu | Leu | Ala | Met | Asn | His | Leu | Gly | Asp |
| 65  |     |     |     |     | 70  |     |     |     |     | 75  |     |     |     |     | 80  |
| Met | Thr | Ser | Glu | Glu | Val | Val | Gln | Lys | Met | Thr | Gly | Leu | Lys | Val | Pro |
|     |     |     |     | 85  |     |     |     |     | 90  |     |     |     |     | 95  |     |
| Pro | Ser | Arg | Ser | His | Ser | Asn | Asp | Thr | Leu | Tyr | Ile | Pro | Asp | Trp | Glu |
|     |     |     |     | 100 |     |     |     |     | 105 |     |     |     |     | 110 |     |
| Gly | Arg | Thr | Pro | Asp | Ser | Ile | Asp | Tyr | Arg | Lys | Lys | Gly | Tyr | Val | Thr |
|     |     |     | 115 |     |     |     |     | 120 |     |     |     |     | 125 |     |     |
| Pro | Val | Lys | Asn | Gln | Gly | Gln | Cys | Gly | Ser | Cys | Trp | Ala | Phe | Ser | Ser |
|     |     |     | 130 |     |     |     | 135 |     |     |     |     | 140 |     |     |     |
| Val | Gly | Ala | Leu | Glu | Gly | Gln | Leu | Lys | Lys | Lys | Thr | Gly | Lys | Leu | Leu |
| 145 |     |     |     |     | 150 |     |     |     |     | 155 |     |     |     |     | 160 |
| Asn | Leu | Ser | Pro | Gln | Asn | Leu | Val | Asp | Cys | Val | Ser | Glu | Asn | Tyr | Gly |
|     |     |     |     | 165 |     |     |     |     | 170 |     |     |     |     | 175 |     |
| Cys | Gly | Gly | Gly | Tyr | Met | Thr | Asn | Ala | Phe | Gln | Tyr | Val | Gln | Arg | Asn |
|     |     |     | 180 |     |     |     |     | 185 |     |     |     |     | 190 |     |     |
| Arg | Gly | Ile | Asp | Ser | Glu | Asp | Ala | Tyr | Pro | Tyr | Val | Gly | Gln | Asp | Glu |
|     |     |     | 195 |     |     |     |     | 200 |     |     |     |     | 205 |     |     |
| Ser | Cys | Met | Tyr | Asn | Pro | Thr | Gly | Lys | Ala | Ala | Lys | Cys | Arg | Gly | Tyr |
|     | 210 |     |     |     |     | 215 |     |     |     |     | 220 |     |     |     |     |
| Arg | Glu | Ile | Pro | Glu | Gly | Asn | Glu | Lys | Ala | Leu | Lys | Arg | Ala | Val | Ala |
| 225 |     |     |     |     | 230 |     |     |     |     | 235 |     |     |     |     | 240 |
| Arg | Val | Gly | Pro | Val | Ser | Val | Ala | Ile | Asp | Ala | Ser | Leu | Thr | Ser | Phe |
|     |     |     |     | 245 |     |     |     |     | 250 |     |     |     |     | 255 |     |
| Gln | Phe | Tyr | Ser | Lys | Gly | Val | Tyr | Tyr | Asp | Glu | Asn | Cys | Ser | Ser | Asp |
|     |     |     | 260 |     |     |     |     | 265 |     |     |     |     | 270 |     |     |
| Asn | Val | Asn | His | Ala | Val | Leu | Ala | Val | Gly | Tyr | Gly | Ile | Gln | Lys | Gly |
|     |     | 275 |     |     |     |     | 280 |     |     |     |     | 285 |     |     |     |
| Asn | Lys | His | Trp | Ile | Ile | Lys | Asn | Ser | Trp | Gly | Glu | Ser | Trp | Gly | Asn |
|     | 290 |     |     |     |     | 295 |     |     |     |     | 300 |     |     |     |     |
| Lys | Gly | Tyr | Ile | Leu | Met | Ala | Arg | Asn | Lys | Asn | Asn | Ala | Cys | Gly | Ile |
| 305 |     |     |     |     | 310 |     |     |     |     | 315 |     |     |     |     | 320 |
| Ala | Asn | Leu | Ala | Ser | Phe | Pro | Lys | Met |     |     |     |     |     |     |     |
|     |     |     |     | 325 |     |     |     |     |     |     |     |     |     |     |     |

( 2 ) INFORMATION FOR SEQ ID NO:4:

( i ) SEQUENCE CHARACTERISTICS:
        ( A ) LENGTH: 331 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:4:

|     |     |     |     |     |     |     |     |     |     |     |     |     |     |     |     |
|---|---|---|---|---|---|---|---|---|---|---|---|---|---|---|---|
| Met | Lys | Arg | Leu | Val | Cys | Val | Leu | Leu | Val | Cys | Ser | Ser | Ala | Val | Ala |
| 1   |     |     |     | 5   |     |     |     |     | 10  |     |     |     |     | 15  |     |
| Gln | Leu | His | Lys | Asp | Pro | Thr | Leu | Asp | His | His | Trp | His | Leu | Trp | Lys |
|     |     |     | 20  |     |     |     |     | 25  |     |     |     |     | 30  |     |     |
| Lys | Thr | Tyr | Gly | Lys | Gln | Tyr | Lys | Glu | Lys | Asn | Glu | Glu | Ala | Val | Arg |
|     |     | 35  |     |     |     |     | 40  |     |     |     |     | 45  |     |     |     |
| Arg | Leu | Ile | Trp | Glu | Lys | Asn | Leu | Lys | Phe | Val | Met | Leu | His | Asn | Leu |
|     | 50  |     |     |     |     | 55  |     |     |     |     | 60  |     |     |     |     |
| Glu | His | Ser | Met | Gly | Met | His | Ser | Tyr | Asp | Leu | Gly | Met | Asn | His | Leu |
| 65  |     |     |     |     | 70  |     |     |     |     | 75  |     |     |     |     | 80  |

```
Gly Asp Met Thr Ser Glu Glu Val Met Ser Leu Met Ser Ser Leu Arg
                85              90                  95
Val Pro Ser Gln Trp Gln Arg Asn Ile Thr Tyr Lys Ser Asn Pro Asn
            100             105             110
Arg Ile Leu Pro Asp Ser Val Asp Trp Arg Glu Lys Gly Cys Val Thr
        115             120             125
Glu Val Lys Tyr Gln Gly Ser Cys Gly Ala Cys Trp Ala Phe Ser Ala
    130             135             140
Val Gly Ala Leu Glu Ala Gln Leu Lys Leu Lys Thr Gly Lys Leu Val
145             150             155                 160
Ser Leu Ser Ala Gln Asn Leu Val Asp Cys Ser Thr Glu Lys Tyr Gly
                165             170             175
Asn Lys Gly Cys Asn Gly Gly Phe Met Thr Thr Ala Phe Gln Tyr Ile
            180             185             190
Ile Asp Asn Lys Gly Ile Asp Ser Asp Ala Ser Tyr Pro Tyr Lys Ala
        195             200             205
Met Asp Gln Lys Cys Gln Tyr Asp Ser Lys Tyr Arg Ala Ala Thr Cys
    210             215             220
Ser Lys Tyr Thr Glu Leu Pro Tyr Gly Arg Glu Val Asp Leu Lys Glu
225             230             235                 240
Ala Val Ala Asn Lys Gly Pro Val Ser Val Gly Val Asp Ala Arg His
            245             250             255
Pro Ser Phe Phe Leu Tyr Arg Ser Gly Val Tyr Tyr Glu Pro Ser Cys
            260             265             270
Thr Gln Asn Val Asn His Gly Val Leu Val Val Gly Tyr Gly Asp Leu
        275             280             285
Asn Gly Lys Glu Tyr Trp Leu Val Lys Asn Ser Trp Gly His Asn Phe
    290             295             300
Gly Glu Glu Gly Tyr Ile Arg Met Ala Arg Asn Lys Gly Asn His Cys
305             310             315                 320
Gly Ile Ala Ser Phe Pro Ser Tyr Pro Glu Ile
            325             330
```

( 2 ) INFORMATION FOR SEQ ID NO:5:

( i ) SEQUENCE CHARACTERISTICS:
( A ) LENGTH: 333 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:5:

```
Met Asn Pro Thr Leu Ile Leu Ala Ala Phe Cys Leu Gly Ile Ala Ser
1               5                   10                  15
Ala Thr Leu Thr Phe Asp His Ser Leu Glu Ala Gln Trp Thr Lys Trp
            20              25              30
Lys Ala Met His Asn Arg Leu Tyr Gly Met Asn Glu Glu Gly Trp Arg
        35              40              45
Arg Ala Val Trp Glu Lys Asn Met Lys Met Ile Glu Leu His Asn Gln
    50              55              60
Glu Tyr Arg Glu Gly Lys His Ser Phe Thr Met Ala Met Asn Ala Phe
65              70              75                  80
Gly Asp Met Thr Ser Glu Glu Phe Arg Gln Val Met Asn Gly Phe Gln
                85              90                  95
```

```
Asn Arg Lys Pro Arg Lys Gly Lys Val Phe Gln Glu Pro Leu Phe Tyr
            100             105                 110
Glu Ala Pro Arg Ser Val Asp Trp Arg Glu Lys Gly Tyr Val Thr Pro
            115             120                 125
Val Lys Asn Gln Gly Gln Cys Gly Ser Cys Trp Ala Phe Ser Ala Thr
    130             135                 140
Gly Ala Leu Glu Gly Gln Met Phe Arg Lys Thr Gly Arg Leu Ile Ser
145             150                 155                         160
Leu Ser Glu Gln Asn Leu Val Asp Cys Ser Gly Pro Gln Gly Asn Glu
                165                 170                 175
Gly Cys Asn Gly Gly Leu Met Asp Tyr Ala Phe Gln Tyr Val Gln Asp
            180                 185                 190
Asn Gly Gly Leu Asp Ser Glu Glu Ser Tyr Pro Tyr Glu Ala Thr Glu
        195                 200                 205
Glu Ser Cys Lys Tyr Asn Pro Lys Tyr Ser Val Ala Asn Asp Thr Gly
    210                 215                 220
Phe Val Asp Ile Pro Lys Gln Glu Lys Ala Leu Met Lys Ala Val Ala
225             230                 235                         240
Thr Val Gly Pro Ile Ser Val Ala Ile Asp Ala Gly His Glu Ser Phe
                245                 250                 255
Leu Phe Tyr Lys Glu Gly Ile Tyr Phe Glu Pro Asp Cys Ser Ser Glu
            260                 265                 270
Asp Met Asp His Gly Val Leu Val Val Gly Tyr Gly Phe Glu Ser Thr
        275                 280                 285
Glu Ser Asp Asn Asn Lys Tyr Trp Leu Val Lys Asn Ser Trp Gly Glu
    290                 295                 300
Glu Trp Gly Met Gly Gly Tyr Val Lys Met Ala Lys Asp Arg Arg Asn
305             310                 315                         320
His Cys Gly Ile Ala Ser Ala Ala Ser Tyr Pro Thr Val
                325                 330
```

( 2 ) INFORMATION FOR SEQ ID NO:6:

( i ) SEQUENCE CHARACTERISTICS:
      ( A ) LENGTH: 335 amino acids
      ( B ) TYPE: amino acid
      ( C ) STRANDEDNESS: unknown
      ( D ) TOPOLOGY: unknown ( i i ) MOLECULE TYPE: protein ( x i ) SEQUENCE DESCRIPTION: SEQ ID NO:6:

```
Met Trp Ala Thr Leu Pro Leu Leu Cys Ala Gly Ala Trp Leu Leu Cys
1               5                   10                  15
Val Pro Val Cys Gly Ala Ala Glu Leu Cys Val Asn Ser Leu Glu Lys
            20                  25                  30
Phe His Phe Lys Ser Trp Met Ser Lys His Arg Lys Thr Tyr Ser Thr
        35                  40                  45
Glu Glu Tyr His His Arg Leu Gln Thr Phe Ala Ser Asn Trp Arg Lys
    50                  55                  60
Ile Asn Ala His Asn Asn Gly Asn His Thr Phe Lys Met Ala Leu Asn
65                  70                  75                      80
Gln Phe Ser Asp Met Ser Phe Ala Glu Ile Lys His Lys Tyr Leu Trp
                85                  90                  95
Ser Glu Pro Gln Asn Cys Ser Ala Thr Lys Ser Asn Tyr Leu Arg Gly
            100                 105                 110
Thr Gly Pro Tyr Pro Pro Ser Val Asp Trp Arg Lys Lys Gly Asn Phe
```

|     |     |     |     |     | 115 |     |     |     |     | 120 |     |     |     |     | 125 |     |     |
| --- | --- | --- | --- | --- | --- | --- | --- | --- | --- | --- | --- | --- | --- | --- | --- | --- | --- |
| Val | Ser | Pro | Val | Lys | Asn | Gln | Gly | Ala | Cys | Gly | Ser | Cys | Trp | Thr | Phe |
|     |     | 130 |     |     |     |     | 135 |     |     |     |     | 140 |     |     |     |
| Ser | Thr | Thr | Gly | Ala | Leu | Glu | Ser | Ala | Ile | Ala | Ile | Ala | Thr | Gly | Lys |
|     |     | 145 |     |     |     | 150 |     |     |     |     | 155 |     |     |     | 160 |
| Met | Leu | Ser | Leu | Ala | Glu | Gln | Gln | Leu | Val | Asp | Cys | Ala | Gln | Asp | Phe |
|     |     |     |     |     | 165 |     |     |     | 170 |     |     |     |     | 175 |     |
| Asn | Asn | Tyr | Gly | Cys | Gln | Gly | Gly | Leu | Pro | Ser | Gln | Ala | Phe | Glu | Tyr |
|     |     |     | 180 |     |     |     |     | 185 |     |     |     |     | 190 |     |     |
| Ile | Leu | Tyr | Asn | Lys | Gly | Ile | Met | Gly | Glu | Asp | Thr | Tyr | Pro | Tyr | Gln |
|     |     | 195 |     |     |     |     | 200 |     |     |     |     | 205 |     |     |     |
| Gly | Lys | Asp | Gly | Tyr | Cys | Lys | Phe | Gln | Pro | Gly | Lys | Ala | Ile | Gly | Phe |
|     |     | 210 |     |     |     |     | 215 |     |     |     |     | 220 |     |     |     |
| Val | Lys | Asp | Val | Ala | Asn | Ile | Thr | Ile | Tyr | Asp | Glu | Glu | Ala | Met | Val |
|     |     | 225 |     |     |     | 230 |     |     |     |     | 235 |     |     |     | 240 |
| Glu | Ala | Val | Ala | Leu | Tyr | Asn | Pro | Val | Ser | Phe | Ala | Phe | Glu | Val | Thr |
|     |     |     |     |     | 245 |     |     |     | 250 |     |     |     |     | 255 |     |
| Gln | Asp | Phe | Met | Met | Tyr | Arg | Thr | Gly | Ile | Tyr | Ser | Ser | Thr | Ser | Cys |
|     |     |     |     | 260 |     |     |     |     | 265 |     |     |     | 270 |     |     |
| His | Lys | Thr | Pro | Asp | Lys | Val | Asn | His | Ala | Val | Leu | Ala | Val | Gly | Tyr |
|     |     | 275 |     |     |     |     | 280 |     |     |     |     | 285 |     |     |     |
| Gly | Glu | Lys | Asn | Gly | Ile | Pro | Tyr | Trp | Ile | Val | Lys | Asn | Ser | Trp | Gly |
|     |     | 290 |     |     |     |     | 295 |     |     |     |     | 300 |     |     |     |
| Pro | Gln | Trp | Gly | Met | Asn | Gly | Tyr | Phe | Leu | Ile | Glu | Arg | Gly | Lys | Asn |
| 305 |     |     |     |     | 310 |     |     |     |     | 315 |     |     |     |     | 320 |
| Met | Cys | Gly | Leu | Ala | Ala | Cys | Ala | Ser | Tyr | Pro | Ile | Pro | Leu | Val |
|     |     |     |     |     | 325 |     |     |     | 330 |     |     |     |     | 335 |

( 2 ) INFORMATION FOR SEQ ID NO:7:

( i ) SEQUENCE CHARACTERISTICS:
        ( A ) LENGTH: 339 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:7:

| Met | Trp | Gln | Leu | Trp | Ala | Ser | Leu | Cys | Cys | Leu | Leu | Val | Leu | Ala | Asn |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Ala | Arg | Ser | Arg | Pro | Ser | Phe | His | Pro | Val | Ser | Asp | Glu | Leu | Val | Asn |
|     |     |     | 20 |     |     |     | 25 |     |     |     |     | 30 |     |     |     |
| Tyr | Val | Asn | Lys | Arg | Asn | Thr | Thr | Trp | Gln | Ala | Gly | His | Asn | Phe | Tyr |
|     |     | 35 |     |     |     |     | 40 |     |     |     |     | 45 |     |     |     |
| Asn | Val | Asp | Met | Ser | Tyr | Leu | Lys | Arg | Leu | Cys | Gly | Thr | Phe | Leu | Gly |
|     | 50 |     |     |     |     | 55 |     |     |     |     | 60 |     |     |     |     |
| Gly | Pro | Lys | Pro | Pro | Gln | Arg | Val | Met | Phe | Thr | Glu | Asp | Leu | Lys | Leu |
| 65 |     |     |     |     | 70 |     |     |     |     | 75 |     |     |     |     | 80 |
| Pro | Ala | Ser | Phe | Asp | Ala | Arg | Glu | Gln | Trp | Pro | Gln | Cys | Pro | Thr | Ile |
|     |     |     |     | 85 |     |     |     |     | 90 |     |     |     |     | 95 |     |
| Lys | Glu | Ile | Arg | Asp | Gln | Gly | Ser | Cys | Gly | Ser | Cys | Trp | Ala | Phe | Gly |
|     |     |     | 100 |     |     |     |     | 105 |     |     |     |     | 110 |     |     |
| Ala | Val | Glu | Ala | Ile | Ser | Asp | Arg | Ile | Cys | Ile | His | Thr | Asn | Ala | His |
|     |     |     | 115 |     |     |     |     | 120 |     |     |     |     | 125 |     |     |
| Val | Ser | Val | Glu | Val | Ser | Ala | Glu | Asp | Leu | Leu | Thr | Cys | Cys | Gly | Ser |
|     |     | 130 |     |     |     |     | 135 |     |     |     |     | 140 |     |     |     |

```
Met  Cys  Gly  Asp  Gly  Cys  Asn  Gly  Gly  Tyr  Pro  Ala  Glu  Ala  Trp  Asn
145                      150                      155                      160

Phe  Trp  Thr  Arg  Lys  Gly  Leu  Val  Ser  Gly  Leu  Tyr  Glu  Ser  His
                    165                      170                      175

Val  Gly  Cys  Arg  Pro  Tyr  Ser  Ile  Pro  Pro  Cys  Glu  His  His  Val  Asn
               180                      185                      190

Gly  Ser  Arg  Pro  Pro  Cys  Thr  Gly  Glu  Gly  Asp  Thr  Pro  Lys  Cys  Ser
          195                      200                      205

Lys  Ile  Cys  Glu  Pro  Gly  Tyr  Ser  Pro  Thr  Tyr  Lys  Gln  Asp  Lys  His
     210                      215                      220

Tyr  Gly  Tyr  Asn  Ser  Tyr  Ser  Val  Ser  Asn  Ser  Glu  Lys  Asp  Ile  Met
225                      230                      235                      240

Ala  Glu  Ile  Tyr  Lys  Asn  Gly  Pro  Val  Glu  Gly  Ala  Phe  Ser  Val  Tyr
                    245                      250                      255

Ser  Asp  Phe  Leu  Leu  Tyr  Lys  Ser  Gly  Val  Tyr  Gln  His  Val  Thr  Gly
               260                      265                      270

Glu  Met  Met  Gly  Gly  His  Ala  Ile  Arg  Ile  Leu  Gly  Trp  Gly  Val  Glu
          275                      280                      285

Asn  Gly  Thr  Pro  Tyr  Trp  Leu  Val  Ala  Asn  Ser  Trp  Asn  Thr  Asp  Trp
     290                      295                      300

Gly  Asp  Asn  Gly  Phe  Phe  Lys  Ile  Leu  Gly  Gly  Gln  Asp  His  Cys  Gly
305                      310                      315                      320

Ile  Glu  Ser  Glu  Val  Val  Ala  Gly  Ile  Pro  Arg  Thr  Asp  Gln  Tyr  Trp
               325                      330                      335

Glu  Lys  Ile
```

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:8:

GGATACGTTA CNCCNGT                                                                17

( 2 ) INFORMATION FOR SEQ ID NO:9:

( i ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:9:

GCCATGAGRT ANCC                                                                   14

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:10:

CTGGATCCCT GTACCCTGAG GAGATACTG  29

( 2 ) INFORMATION FOR SEQ ID NO:11:

( i ) SEQUENCE CHARACTERISTICS:
    ( A ) LENGTH: 33 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:11:

CTAAGCTTCT ATCTACCTTC CCATTCTGGG ATA  33

CATHESPIN O PROTEASE

FIELD OF THE INVENTION

The invention relates to cathepsin O proteins, nucleic acids, and antibodies.

BACKGROUND OF THE INVENTION

The cathepsins belong to the papain superfamily of cysteine proteases. Cysteine or thiol proteases contain a cysteine residue, as well as a histidine and an asparagine, at the active site responsible for proteolysis. This superfamily also has a glutamine at the oxy-anion hole.

Recent work has implicated cysteine proteases in binding to DNA with putative transcription factor activity (Xu et al., J. Biol. Chem. 269(33): 21177–21183 (1994)), and as a long term immunosuppressor (Hamajima et al., Parasite Immunology 16: 261 (1994)).

To date, a number of cathepsins have been identified and sequenced from a number of animals. For example, cathepsin S has been cloned from rat (Petanceska et al., J. Biol. Chem. 267: 26038–20643 (1992)), bovine (Wideranders et al., FEBS Lett. 286: 189–192 (1991)) and humans (Wiederanders et al., J. Biol. Chem. 267: 13708–13713 (1992); and Shi et al., J. Biol. Chem. 267: 7258– 7262 (1992)). Cathepsin L has been cloned from humans, rat, mouse and chicken (Gal et al. Biochem. J., 253: 303–306 (1988); Ishidoh et al., FEBS Lett. 223: 69–73 (1987); Joseph et al., J. Clin. Invest. 81: 1621–1629 (1988); Ritonja et al., FEBS Lett. 283: 329–331 (1991)). Cathepsin H has been cloned from human and rat (Fuch et al., Biol. Chem. Hoppe-Seyler 369–375 (1988); Fuchs et al., Nucleic Acid Res. 17: 9471 (1989); Whittier et al., Nucleic Acid Res. 15: 2515–2535 (1987)). Cathepsin B has been cloned from human and mouse (Ferrara et al., FEBS Lett. 273: 195–199 (1990); Chan et al., Proc. Natl. Acad. Sci. USA 83: 7721–7725 (1986)).

A cysteine protease from rabbit osteoclasts was recently cloned, and is structurally related to cathepsins L and S. Tezuka et al., J. Biol. Chem. 269(2): 1106 (1994).

Cathepsins are naturally found in a wide variety of tissues. For example, cathepsin L is found in tissues including heart, brain, placenta, lung, skeletal muscle, kidney, liver, testis and pancreas. Cathepsin S is found in lung, liver, spleen and skeletal muscle.

Cathepsins have been implicated in a number of disease conditions. For example, enzymes similar to cathepsins B and L are released from tumors and may be involved in tumor metastasis. Cathepsin L is present in diseased human synovial fluid and transformed tissues. Similarly, the release of cathepsin B and other lysosomal proteases from polymorphonuclear granulocytes and macrophages is observed in trauma and inflammation. Cathepsins have been implicated in arthritis. In addition, cathepsins are found in abnormally high amounts in several tumor cell lines.

Cysteine proteases have also been implicated in bone remodeling. Bone remodeling is a process coupling bone formation and bone resorption, and is part of bone growth. The solid state of bone material is due to the low solubility of hydroxyapatite and other calcium-phosphate bone salts at physiological pH, but bone may break down at acidic pH.

Osteoclasts are multinucleate giant cells that play key roles in bone resorption. Attached to the bone surface, osteoclasts produce an acidic microenvironment in a tightly defined junction between the specialized osteoclast border membrane and the bone matrix, thus allowing the localized solubilization of bone matrix. This in turn facilitates the proteolysis of demineralized bone collagen.

Cysteine protease inhibitors have been shown to inhibit osteoclastic bone resorption by inhibiting degradation of collagen fibers. Cathepsins B, L, N and S can degrade type-I collagen at acidic pH. Three cathepsin-type proteases have been isolated from mouse calvaria; putative cathepsins B and L, and a cathepsin L-like protease (Delaisse et al., Biochem. J. 279: 167 (1991). However, it is still unclear as to what cysteine proteases are actually produced by osteoclasts.

SUMMARY OF THE INVENTION

It is an object of the present invention to provide for a new class of recombinant cathepsins, cathepsin O, and variants thereof, and to produce useful quantities of these cathepsin O proteins using recombinant DNA techniques.

It is a further object of the invention to provide recombinant nucleic acids encoding cathepsin O proteins, and expression vectors and host cells containing the nucleic acid encoding the cathepsin O protein.

An addition object of the invention is to provide poly- and monoclonal antibodies for the detection of the presence of cathepsin O and diagnosis of conditions associated to cathepsin O.

A further object of the invention is to provide methods for producing the cathepsin O proteins.

In accordance with the foregoing objects, the present invention provides recombinant cathepsin O proteins, and isolated or recombinant nucleic acids which encode the cathepsin O proteins of the present invention. Also provided are expression vectors which comprise DNA encoding a cathepsin O protein operably linked to transcriptional and translational regulatory DNA, and host cells which contain the expression vectors.

Additional aspect of the present invention provides methods for producing cathepsin O proteins which comprise culturing a host cell transformed with an expression vector and causing expression of the nucleic acid encoding the cathepsin O protein to produce a recombinant cathepsin O protein.

A further aspect of the present invention provides poly- and monoclonal antibodies to cathepsin O proteins.

BRIEF DESCRIPTION OF THE DRAWINGS

FIGS. 1A and 1B depict the nucleotide sequence (SEQ ID NO:1) and deduced amino acid sequence (SEQ ID NO:2) of human cathepsin O cDNA. The amino acid sequence (SEQ ID NO:2) is shown in single letter code beneath the nucleotide sequence (SEQ ID NO:1). The active site residues (C25, H159 and N175; papain numbering) are indicated by boldface typing, and the potential N-glycosylation site is underlined once. Arrowheads show the putative post-translational cleavage sites between the presignal and the proregion as well as between the proregion and the mature enzyme. The cleavage between the proregion and the mature protein was confirmed by protein sequencing (double underline).

FIGS. 2A and 2B depict the multiple amino acid sequence alignment of human cathepsin O (SEQ ID NO:2) with the human cathepsins S (SEQ ID NO:4) and L (SEQ ID NO:5) and rabbit OC2 (SEQ ID NO:3). * active site residues; boldface type, residue conserved in all known cysteine proteases of the papain family. Amino acids identical in all six proteases are assigned as upper case letters in the consensus sequence, and amino acids identical in five out of six are assigned in lower case letters. Gaps are indicated by hyphens. Numbers indicate the position of the last amino acid in each line and arrowheads show the putative post-translational cleavage sites.

FIG. 3 depicts the pH profile of in vitro activation of recombinant human cathepsin O. The lysed cell extract was incubated at 40° C. in the pH range between 3.0 and 6.5. After time intervals the activity was measured against 10 µM Z-FR-MCA. For details see the examples.

FIG. 4 depicts the SDS-PAGE of purified recombinant human cathepsin O (4–12% Tris-glycine; Coomassie staining). Lane 1, molecular weight standard; lane 2, crude cell extract prior to activation; lane 3, loading material onto Mono S, lane 4, fraction after second passage through Mono S. Molecular weight standards (kDa) are indicated in the left margin.

FIG. 5 depicts the pH activity profile for recombinant human cathepsin O. The relative rates of hydrolysis were calculated from $k_{cat}/K_m$ values obtained from initial rates of Z-FR-MCA hydrolysis and divided by enzyme and substrate concentration. The pH activity profile of human cathepsin S is displayed as a dashed line.

FIG. 6 depicts the pH stability of recombinant human cathepsin O. Purified cathepsin O was incubated at 37° C. in the pH range of 3.5 to 6.5. After time intervals the activity was measured using 10 µM Z-FR-MCA as substrate. For details see the examples.

FIG. 7 depicts a western blot analysis of human cathepsin O. Lane 1, brain; lane 2, heart; lane 3, kidney; lane 4, lung; lane 5, skeletal muscle; lane 6, liver. Polyclonal antibodies raised against purified human cathepsin O were used for detection.

FIG. 8 depicts northern blot analyses of the human cathepsins O, I and S in osteoclastoma preparations. Lane 1, patient (fibrous and cellular tissue); lane 2, patient 2 (cellular tissue); lane 3, patient 2 (fibrous tissue). Nitrocellulose blots were hybridized with 32P-labelled probes of human cathepsins O, L and S.

FIG. 9 depicts an SDS-PAGE (4–20% Tris-glycine) of the collagen (type I) digest by human cathepsins O, L S and Clostridium collagenase. Lane 1, Collagen, pH 4.0; lane 2: NCAT5, pH 4.0; lane 3: RCATL, pH 4.0; lane 4: HCATO, pH 4.0; lane 5: HCAT5, pH 5.0; lane 6: RCATL, pH 5.0; lane 7: HCATO, pH 5.0; lane 8: Collagenase, pH 8.0; lane 9: Collagen, pH 5.0; lane 10: molecular weight standard (kDa). Arrowheads mark the triple helix trimer, dimer and monomers of collagen type I.

FIG. 10 depicts an SDS-PAGE of the purification of the propart of human cathepsin O.

DETAILED DESCRIPTION OF THE INVENTION

The present invention provides novel cathepsin O proteins and nucleic acids.

The cathepsin O proteins of the present invention may be identified in several ways. Cathepsin O nucleic acids or cathepsin O proteins are initially identified by substantial nucleic acid and/or amino acid sequence homology to the sequences shown in FIG. 1. Such homology can be based upon the overall nucleic acid or amino acid sequence.

The cathepsin O proteins of the present invention have limited homology to other cathepsins. For example, the mature human cathepsin O has roughly 59% homology to mature human cathepsin L, a 58% homology to mature human cathepsin S, a 26% homology to mature human cathepsin B, and a 47% homology to mature human cathepsin H. In addition, the propart of human cathepsin O has a 38% homology to the propart of human cathepsin L, a 51% homology to the propart of human cathepsin S, a 13% homology to the propart of human cathepsin B, and a 23% homology to the propart of human cathepsin H. In addition, the human cathepsin O protein has roughly 90% homology to a rabbit osteoclast protein.

As used herein, a protein is a "cathepsin O protein" if the overall homology of the protein sequence to the amino acid sequence shown in FIG. 1 is preferably greater than about 90%, more preferably greater than about 95% and most preferably greater than 98%. This homology will be determined using standard techniques known in the art, such as the Best Fit sequence program described by Devereux et al., Nucl. Acid Res. 12: 387–395 (1984). The alignment may include the introduction of gaps in the sequences to be aligned. In addition, for sequences which contain either more or fewer amino acids than the protein shown in FIG. 1, it is understood that the percentage of homology will be determined based on the number of homologous amino acids in relation to the total number of amino acids. Thus, for example, homology of sequences shorter than that shown in FIG. 1, as discussed below, will be determined using the number of amino acids in the shorter sequence.

In a preferred embodiment, the cathepsin O proteins of the present invention are human cathepsin O proteins.

Cathepsin O proteins of the present invention may be shorter than the amino acid sequence shown in FIG. 1. As shown in Example 2, the human cathepsin O protein may undergo post-translational processing similar to that seen for cathepsins B and S, and papain (Brömme et al., J. Biol. Chem. 268: 4832–4838 (1993); Vernat et al., J. Biol. Chem. 266: 21451–21457 (1991); and Rowan et al., J. Biol. Chem. 267: 15993–15999 (1992)). The cathepsin O protein is made as a preproprotein, with a traditional presequence, a prosequence or "propart", and the mature sequence. These are depicted in FIG. 1, with the sequence of human cathepsin O, including the pre, pro and mature coding sequences. The presequence comprises the first 15 amino acids of the sequence shown in FIG. 1, the propart spans from amino acid 16 to amino acid 114 (98 amino acids), and the mature protein spans from position 115 to 329 (215 amino acids). The prosequence, or propart, is hypothesized to serve as an inhibitor of the enzyme until the enzyme is activated, most probably as a result of a change in pH. The proteolytic processing of the propart is thought to occur autolytically, but this is currently speculative, although a similar autoproteolytic process has been shown for papain (Vernet et al., supra). The definition of cathepsin O includes preprocathepsin O, procathepsin O, mature cathepsin O, and the propart, separate from the mature cathepsin O.

In a preferred embodiment, also included within the definition of cathepsin O proteins are portions or fragments of the sequence shown in FIG. 1. In one embodiment, the fragments range from about 40 to about 200 amino acids. Preferably, the fragments are not identical to the rabbit osteoclast protein of Tezuka et al., supra, and at least about 95–98% homologous to the human cathepsin O protein. In a preferred embodiment, when the cathepsin O protein is to be used to generate antibodies, for example for diagnostic purposes, the cathepsin O protein must share at least one epitope or determinant with either the propart or the mature protein shown in FIG. 1. By "epitope" or "determinant" herein is meant a portion of a protein which will generate and bind an antibody. Thus, in most instances, antibodies made to a smaller cathepsin O protein will be able to bind to the full length protein.

In a preferred embodiment, the antibodies are generated to a unique epitope; that is, the antibodies exhibit little or no cross reactivity to other proteins such as other cathepsin proteins, or to cathepsins from other organisms.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequence of FIG. 1 is preferably greater than 65%, more preferably greater than about 75% and most preferably greater than 85%. In some embodiments the homology will be as high as about 95 to 98 or 99%.

The cathepsin O proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Specifically included within the definition of nucleic acid are anti-sense nucleic acids. An anti-sense nucleic acid will hybridize to the corresponding non-coding strand of the nucleic acid sequence shown in FIG. 1, but may contain ribonucleotides as well as deoxyribonucleotides. Generally, anti-sense nucleic acids function to prevent expression of mRNA, such that a cathepsin O protein is not made. The nucleic acid may be double stranded, single stranded, or contain portions of both double stranded or single stranded sequence.

By the term "recombinant nucleic acid" herein is meant nucleic acid, originally formed in vitro by the manipulation of nucleic acid by endonucleases, in a form not normally found in nature. Thus an isolated cathepsin O protein gene, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host. Thus, for example, cathepsin O proteins which are substantially or partially purified, or are present in the absence of cells, are considered recombinant. The definition includes the production of a cathepsin O protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions.

Also included with the definition of cathepsin O protein are cathepsin O proteins from other organisms, which are cloned and expressed as outlined below.

In the case of anti-sense nucleic acids, an anti-sense nucleic acid is defined as one which will hybridize to all or part of the corresponding non-coding sequence shown in FIG. 1. Generally, the hybridization conditions used for the determination of anti-sense hybridization will be high stringency conditions, such as 0.1 XSSC at 65° C.

Once the cathepsin O protein nucleic acid is identified, it can be cloned and, if necessary, its constituent parts recombined to form the entire cathepsin O protein nucleic acid. Once isolated from its natural source, e.g., contained within a plasmid or other vector or excised therefrom as a linear nucleic acid segment, the recombinant cathepsin O protein nucleic acid can be further used as a probe to identify and isolate other cathepsin O protein nucleic acids. It can also be used as a "precursor" nucleic acid to make modified or variant cathepsin O protein nucleic acids and proteins.

Using the nucleic acids of the present invention which encode cathepsin O protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the cathepsin O protein. "Operably linked" in this context means that the transcriptional and translational regulatory DNA is positioned relative to the coding sequence of the cathepsin O protein in such a manner that transcription is initiated. Generally, this will mean that the promoter and transcriptional initiation or start sequences are positioned 5' to the cathepsin O protein coding region. The transcriptional and translational regulatory nucleic acid will generally be appropriate to the host cell used to express the cathepsin O protein; for example, transcriptional and translational regulatory nucleic acid sequences from Bacillus will be used to express the cathepsin O protein in Bacillus. Numerous types of appropriate expression vectors, and suitable regulatory sequences are known in the art for a variety of host cells.

In general, the transcriptional and translational regulatory sequences may include, but are not limited to, promoter sequences, leader or signal sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The cathepsin O proteins of the present invention are produced by culturing a host cell transformed with an expression vector containing nucleic acid encoding a cathepsin O protein, under the appropriate conditions to induce or cause expression of the cathepsin O protein. The conditions appropriate for cathepsin O protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis,* SF9 cells, C129 cells, 293 cells, Neurospora, BHK, CHO, COS, HeLa cells, and immortalized mammalian myeloid and lymphoid cell lines.

In a preferred embodiment, cathepsin O proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of cathepsin O protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli,* the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the cathepsin O protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, cathepsin O proteins are produced in insect cells. Expression vectors for the transformation of insect cells, and in particular, baculovirus-based expression vectors, are well known in the art. Briefly, baculovirus is a very large DNA virus which produces its coat protein at very high levels. Due to the size of the baculoviral genome, exogenous genes must be placed in the viral genome by recombination. Accordingly, the components of the expression system include: a transfer vector, usually a bacterial plasmid, which contains both a fragment of the baculovirus genome, and a convenient restriction site for insertion of the cathepsin O protein; a wild type baculovirus with a sequence homologous to the baculovirus-specific fragment in the transfer vector (this allows for the homologous recombination of the heterologous gene into the baculovirus genome); and appropriate insect host cells and growth media.

Mammalian expression systems are also known in the art and are used in one embodiment. A mammalian promoter is any DNA sequence capable of binding mammalian RNA polymerase and initiating the downstream (3') transcription of a coding sequence for cathepsin O protein into mRNA. A promoter will have a transcription initiating region, which is usually place proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element, typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, and herpes simplex virus promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, encapsulation of the polynucleotide(s) in liposomes, and direct microinjection of the DNA into nuclei.

In a preferred embodiment, cathepsin O protein is produced in yeast cells. Yeast expression systems are well known in the art, and include expression vectors for *Saccharomyces cerevisiae, Candida albicans* and *C. maltosa, Hansenula polymorpha, Kluyveromyces fraqilis* and *K. lactis, Pichia guillerimondii* and *P. pastoris, Schizosaccharomyces pombe,* and *Yarrowia lipolytica.* Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the G418 resistance gene, which confers resistance to G418; and the CUP1 gene, which allows yeast to grow in the presence of copper ions.

A recombinant cathepsin O protein may be expressed intracellularly or secreted. The cathepsin O protein may also be made as a fusion protein, using techniques well known in the art. Thus, for example, if the desired epitope is small, the cathepsin O protein may be fused to a carrier protein to form an immunogen. Alternatively, the cathepsin O protein may be made as a fusion protein to increase expression, or for other reasons.

Also included within the definition of cathepsin O proteins of the present invention are amino acid sequence variants. These variants fall into one or more of three classes: substitutional, insertional or deletional variants. These variants ordinarily are prepared by site specific mutagenesis of nucleotides in the DNA encoding the cathepsin O protein, using cassette mutagenesis or other techniques well known in the art, to produce DNA encoding the variant, and thereafter expressing the DNA in recombinant cell culture as outlined above. However, variant cathepsin O protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the cathepsin O protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed cathepsin O protein variants screened for the optimal combination of desired activity. Techniques for making substitution mutations at predetermined sites in DNA having a known sequence are well known, for example, M13 primer mutagenesis. Screening of the mutants is done using assays of cathepsin O protein activities; for example, purified or partially purified cathepsin O may be used in kinetic assays such as those depicted in the examples, to determine the effect of the amino acid substitutions, insertions or deletions. Alternatively, mutated cathepsin O genes are placed in cathepsin O deletion strains and tested for cathepsin O activity, as disclosed herein. The creation of deletion strains, given a gene sequence, is known in the art.

Amino acid substitutions are typically of single residues; insertions usually will be on the order of from about 1 to 20 amino acids, although considerably larger insertions may be tolerated. Deletions range from about 1 to 30 residues, although in some cases deletions may be much larger, as for example when the prosequence or the mature part of the cathepsin O protein is deleted. In addition, as outlined above, it is possible to use much smaller fragments of the cathepsin O protein to generate antibodies.

Substitutions, deletions, insertions or any combination thereof may be used to arrive at a final derivative. Generally these changes are done on a few amino acids to minimize the alteration of the molecule. However, larger changes may be tolerated in certain circumstances.

When small alterations in the characteristics of the cathepsin O protein are desired, substitutions are generally made in accordance with the following chart:

Chart I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glue | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the polypeptide as needed. Alternatively, the variant may be designed such that the biological activity of the cathepsin O protein is altered. For example, the proteolytic activity of the cathepsin O protein may be altered, through the substitution of the amino acids of the catalytic triad. The catalytic triad, consisting of a cysteine at position 25, a histidine at position 162 and an asparagine at position 182, may be individually or simultaneously altered to decrease or eliminate proteolytic activity. This may be done to decrease the toxicity of administered cathepsin O. Similarly, the cleavage site between the prosequence and the mature sequence may be altered, for example to eliminate proteolytic processing.

In a preferred embodiment, the cathepsin O protein is purified or isolated after expression. Cathepsin O proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the cathepsin O protein may be purified using a standard anti-cathepsin O antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the cathepsin O protein. In some instances no purification will be necessary.

Once expressed and purified if necessary, the cathepsin O proteins are useful in a number of applications.

For example, as shown in Example 5, the cathepsin O proteins of the present invention have collagenase activity. Thus, the cathepsin O proteins may be used as a collagenase, both in vitro and in vivo. For example, cathepsin O may be used to treat analytical samples which contain interfering or problematic levels of collagen.

Similarly, cathepsin O proteins may be used to degrade excess collagen within the body. There are a variety of conditions associated with excess collagen. For example, one treatment of spinal disk problems such as severe disk inflammation and herniation involves the injection of collagenase or chymopapain to degrade the disk collagen (Leonardo et al., Ann. Chirm Gyneacol. 82: 141–148 (1993); Gogan et al., Spine 17: 388–94 (1992); Stula, Nerochirurgia 33: 169–172 (1990); and Boccanera et al., Chir. Organi. Mov. 75: 25–32 (1990)). Alternatively, the treatment of adhesions, such as pelvic adhesions, post surgical adhesions, pulmonary adhesions, abdominal adhesions and the like may be treated or dissolved with cathepsin O. Similarly, scars and keloids may be treated with cathepsin O to remove or decrease the excessive amounts of collagen present.

In addition, endometriosis is another significant clinical problem involving the deposit of excess amounts of collagen and other substances within the uterus and surrounding tissue; certain forms of endometriosis may also be treated with the cathepsin O of the present invention.

In an alternative embodiment, cathepsin O may be used to dissolve the matrices around tumors. Generally, tumor pH is lower than physiological pH, and, as outlined in the Examples, cathepsin O is active at acidic pH. Therefore, cathepsin O is suited to dissolve the collagen-based matrix generally surrounding a tumor.

In one embodiment, the cathepsin O proteins of the present invention may also be administered to treat pycnodysostosis, an osteopetrosislike bone disorder. This disorder appears to be caused by insufficient activity of osteoclastic cysteine-proteinases. In some embodiments, gene therapy may be used to administer the cathepsin O.

In addition, since cathepsin O is functional at acidic pH, cathepsin O can be administered in conjunction with bone demineralization compounds, such as acids, to degrade bone tissue. Thus, aberrant or excess bone growths may be treated.

The cathepsin O proteins of the present invention are also useful to screen for cathepsin O protease inhibitors and for cysteine protease inhibitors. Cysteine protease inhibitors have a variety of uses, as will be appreciated in the art, including purification of cysteine proteases via coupling to affinity chromatography columns, and inhibition of cysteine proteases, similar to known cysteine protease inhibitors. In addition, cysteine protease inhibitors may have therapeutic uses, since a wide variety of physiological disorders are associated with increased levels of cysteine proteases, including arthritis, inflammation, muscular dystrophy, tumor invasion and glomerulonephritis, as is known in the art.

In a preferred embodiment, the propart of cathepsin O may be used as a specific inhibitor of cathepsin O. Thus, for example, the propart may be separately expressed, that is, without the mature sequence, and used as a highly specific tight-binding inhibitor of cathepsin O, as is shown in Example 3. Thus, the propart may be added therapeutically to samples or tissues which contain excess cathepsin O; for example, in the treatment of bone disorders or tumors, as outlined below.

In one embodiment, the propart of cathepsin O is labeled, and used to diagnose, quantify or identify the presence of cathepsin O within a sample or tissue.

Additionally, the cathepsin O proteins may be used to generate polyclonal and monoclonal antibodies to cathepsin O proteins, which are useful as described below. Similarly, the cathepsin O proteins can be coupled, using standard technology, to affinity chromatography columns. These columns may then be used to purify cathepsin O antibodies.

In a preferred embodiment, monoclonal antibodies are generated to the cathepsin O protein, using techniques well known in the art. As outlined above, the antibodies may be generated to the full length cathepsin O protein, or a portion of the cathepsin O protein.

In a preferred embodiment, the antibodies are generated to epitopes unique to the human cathepsin O protein; that is, the antibodies show little or no cross-reactivity to antibodies generated to cathepsin O proteins from other organisms, such as cathepsins from rabbits or rats.

These antibodies find use in a number of applications. In a preferred embodiment, the antibodies are used to diagnose the presence of cathepsin O in a sample or patient. For example, an excess of cathepsin O protein, such as may exist in osteoclast related disorders and bone diseases, as well as tumors, may be diagnosed using these antibodies.

Similarly, high levels of cathepsin O are associated with certain ovarian or cervical carcinomas, as evidenced by high levels of cathepsin O in HeLa cells. Thus, these types of tumors may be detected or diagnosed using the antibodies of the present invention.

The detection of cathepsin O will be done using techniques well known in the art; for example, samples such as blood or tissue samples may be obtained from a patient and tested for reactivity with labelled cathepsin O antibodies, for example using standard techniques such as RIA and ELISA.

In one embodiment, the antibodies may be directly or indirectly labelled. By "labelled" herein is meant a compound that has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Thus, for example, the cathepsin O protein antibody may be labelled for detection, or a secondary antibody to the cathepsin O protein antibody may be created and labelled.

In one embodiment, the antibodies generated to the cathepsin O proteins of the present invention are used to purify or separate cathepsin O proteins from a sample. Thus for example, antibodies generated to cathepsin O proteins may be coupled, using standard technology, to affinity chromatography columns. These columns can be used to pull out the cathepsin O protein from tissue samples.

Recent work has suggested that cysteine proteases may be used as DNA binding transcription factors (Xu et al., supra). In some embodiments, the cathepsin O proteins of the present invention may be used as transcription factors.

The parasite *Paragonimus westerman* was recently shown to express an immunosuppressor with homology to cysteine proteases (Hamajima et al., supra). In fact, the homology to the cathepsin O proteins of the present invention is roughly 40%. Thus, in one embodiment, the cathepsin O proteins may be useful as immunosuppressors.

In a preferred embodiment, when the cathepsin O proteins are to be administered to a human, the cathepsin O proteins are human cathepsin O proteins. This is therapeutically desirable in order to ensure that undesirable immune reactions to the administered cathepsin O are minimized.

The administration of the cathepsin O protein of the present invention can be done in a variety of ways, including, but not limited to, orally, subcutaneously, intravenously, intranasally, transdermally, intraperitoneally, intramuscularly, intrapulmonary, vaginally, rectally, or intraocularly.

The pharmaceutical compositions of the present invention comprise a cathepsin O protein in a form suitable for administration to a patient. The pharmaceutical compositions may include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The pharmaceutical compositions of the present invention are generally administered at therapeutically effective dosages, as can be routinely determined by those in the art.

It is believed that the human cathepsin O protein of the invention has characteristices which render the human protein more acceptable than cathepsin O proteins from other species for therapeutic purposes. In particular, the antigenicity of cathepsin O proteins from other species in humans makes these proteins less acceptable as therapeutic compositions; i.e. cathepsins from other species may elicit undesirable immunological responses in humans.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. The references cited herein are incorporated by reference.

EXAMPLES

Example 1

Cloning of Human Cathepsin O

Unless otherwise specified, all general recombinant DNA techniques followed the methods described in Sambrook et al. (Molecular Cloning, A Laboratory Manual, Cold Spring Harbor Press, 1989).

Two degenerate PCR primers were designed based on the published sequence of a rabbit osteoclastin gene (Tezuko et al. 1994):

5'—GGA—TAC—GTT—ACN—CCN—GT—3' (SEQ ID NO:8)

5'—GC—CAT—GAG—G/ATA—NCC—3' (SEQ ID NO:8)

These primers were used for screening a human spleen Quick Clone cDNA preparation (Clontech). An amplified 450 base pair fragment was isolated and purified and used as a cDNA probe for screening a human spleen cDNA library (gt10 frm Clontech). 600,000 clones were screened on 20 filters using a technique in which the plaques reform directly on the filter (Woo, Methods Enzymol. 68: 389-395 (1979)). This allows an amplification of the signal from positive plaques allowing for shorter exposure times, thus decreasing background and the visualization of false positives. The filters were washed at moderate stringency conditions: once with 2×SSC, 0.1% SDS at room temperature for 10 min and once with 2×SSC, 0.1% SDS at 68° C. for 20 min.

Phages from two positive plaques were isolated and cloned into the EcoRI site of pBluescript SK+ vector (Stratagene).

One positive clone was completely sequenced on an ABI sequencer model 373A; the sequence (SEQ ID NO:1) is shown in FIG. 1. Sequence alignments of the protein and nucleic acid sequences of human cathepsin O (SEQ ID NOS: 1 and 2), human cathepsin S (SEQ ID NO:4) and human cathepsin L (SEQ ID NO:5) are shown in FIG. 2.

Example 2

Expression of human Cathepsin O

The human cathepsin O cDNA was cloned into the polyhedrin gene of the baculovirus transfer vectors using standard methods. The cDNA encoding the complete open reading frame of the prepro enzyme was inserted into the BglII and BamH1 site of the pVL1392 transfer vector (PharMingen). Recombinant baculoviruses were generated by homologous recombination following co-transfection of the baculovirus transfer vector and linearized AcNPV genomic DNA (PharMingen) into SF9 cells. Following end point dilution human cathepsin O expression is measured in a fluorimetric substrate assay, outlined below.

After in vitro activation of the cell pellet and the media supernatant, separately, roughly 60% of the cathepsin O was found intracellularly, and roughly 40% extracellularly.

Activation of recombinant human cathepsin O:

The intracellular cathepsin O was produced within the SF9 cells as an inactive precursor. The enzyme was activated in the cell lysate under reducing and acidic conditions as follows. The cell pellet of SF9 cells expressing cathepsin O was lysed with a dounce homogenizer (15 strokes on ice) and adjusted with 100 mM sodium acetate buffer containing 5 mM dithioerythreitol and 5 mM EDTA to pH 4.0. The mixture was shaken for 5 hours at 40° C. The course of activation was followed in a fluorimetric substrate assay using 10 μM Z—phe—arg—MCA as the substrate. The results are shown in FIG. 4.

Purification of recombinant human cathepsin O

The concentrated media supernatant containing active cathepsin O and the lysed and activated cell extract were combined and cleared by centrifugation. The clear supernatant was further concentrated and applied to a FPLC Mono S ion-exchange chromatographic column. Recombinant human cathepsin O activity was eluted at pH 5.0 in 20 mM sodium acetate buffer using a 0 to 0.3M NaCl gradient. Cathepsin O was purified by reapplying the pooled active fractions to the FPLC Mono S column, and elution with a 0 to 0.2M NaCl gradient in 20 mM sodium acetate, pH 5.0. The collected fraction were tested in a fluorimetric substrate assay. The total yield from 1 liter SF9 culture was approximately 1 mg purified enzyme (50% yield).

N-terminal sequencing of the first 37 amino acids of the protein revealed a homologous contaminant. The contaminant appears to be roughly 80% homologous to the first 37 amino acids of human cathepsin O. The contaminant was traced to the SF9 cells used to express the human cathepsin O. The level of contamination appeared to be up to roughly 50%.

Purification of recombinant human cathepsin O

| step | total protein (mg) | total activity µmol/min | specific activity µmol/min/mg | purification factor | yield |
|---|---|---|---|---|---|
| crude before activation | 959 | 48,000 | — | — | — |
| crude after activation | 336 | 1,108,000 | 128 | 1 | 100 |
| UF-10 | 15.6 | 720,000 | 1,798 | 14 | 65 |
| Mono-S (1) | 3.2 | 640,000 | 7,792 | 61 | 58 |
| Mono-S (2) | 2.5 | 600,000 | 9,425 | 74 | 54 |

Fluorimetric enzyme assay

Human cathepsin O was assayed with a fluorogenic substrate Z—FR—MCA (MCA, ethyl coumarylamide) in 100 mM sodium acetate buffer, containing 5 mM dithioerythreitol and 5 mM EDTA. Initial rates of hydrolysis of the MCA-substrate are monitored in 1-cm cuvettes at 25° C. at an excitation wavelength at 380 nm and an emission wavelength at 450 nm. The concentration of Z—FR—MCA is 5 µM under standard conditions.

Example 3

Cloning and Expression of the propart of cathepsin O

The propart of human cathepsin O was amplified by PCR using standard techniques using the following primers:

5'—CTG GAT CCC TGT ACC CTG AGG AGA TAC TG—3' (SEQ ID NO:10)

5'—CTA AGC TTC TAT CTA CCT TCC CAT TCT GGG ATA—3' (SEQ ID NO:11)

The proregion was expressed in the pTrcHis vector (Invitrogen Corp., San Diego, Calif.), which contains a series of six histidine residues that function as a metal binding domain in the translated protein. This metal binding domain was used to purify the propart of cathepsin O over Invitrogen's ProBond Resin included in their Xpress system Protein Expression kit. A gel of the purified propart is shown in FIG. 10.

The purified propart inhibited the parent enzyme with a $K_i$ value of 0.1 nM.

Example 4

Antibodies to human Cathepsin O

Electrophoretically homogenous mature human cathepsin O, inactivated at neutral pH in 1×PBS, was used to produce polyclonal antibodies in New Zealand white rabbits, and can be used to make monoclonal antibodies in mice by standard techniques. Similarly, polyclonal antibodies against the electrophoretically homogenous propart of human cathepsin O are produced in New Zealand white rabbits, and monoclonal antibodies in mice by standard techniques.

Polyclonal antibodies made to the mature protein were specific for human cathepsin O, and did not exhibit cross-reactivity with human cathepsins S and B, rat cathepsin L nor papain.

Example 5

Characterization of human cathepsin O

The following experiments were done with the partially purified human cathepsin O of example 2.

pH-stability of recombinant human cathepsin O

The pH-stability of cathepsin O was determined by incubation of the active protease at different pH values in presence of 5mM dithioerythreitol and 5mM EDTA at 37° C. The residual activity was measured in time intervals using the above described fluorimetric substrate assay.

Cathepsin O displays its highest pH-stability at pH 4.6. It is extremely pH labile at pH values higher than pH 6.0 (FIG. 5). Cathepsin O is the most unstable mammalian cysteine protease known. This enzyme was instantly inactivated at pH 6.6, whereas cathepsin L is instantly inactivated at pH 7.7.

pH-optimum of recombinant human cathepsin O

A pH-activity profile reveals information about the pH optimum of activity for the hydrolysis of substrates and about functional residues involved in the catalysis. The pH-activity profile was obtained at 1 µM substrate (Z—FR—MCA) concentration ($|S|<<K_m$ where the initial rate $v_o$ is directly proportional to the $k_{cat}/K_m$ value).

The following buffers were used for the pH activity profile: 90 mM sodium citrate (pH 3.0–5.6), 90 mM sodium phosphate (pH 5.8–8.0) and sodium borate (pH 8.0–9.2). All buffers contained 1 mM EDTA and 0.4M NaCl to minimize the variation in ionic strength. For the least square regression analysis of the pH activity data a four-protonation state model (Menard et al., Biochemistry 29: 6706–6713 (1990)) was used (equation 2).

equation(2)

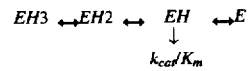

|  | pK1' | pK1 | pK2 | pH-optimum |
|---|---|---|---|---|
| HCATO | 2.89 ± 0.3 | 3.75 ± 0.07 | n.d. | 5.5 |
| RCATL* | 3.33 ± 0.2 | 4.22 ± 0.28 | n.d. | 5.5 |
| HCATS* | — | 4.47 ± 0.03 | 7.9 ± 0.3 | 6.5 |

*Brömme et al., 1993

The pH optimum for the hydrolysis of synthetic substrates was 5.5 for human cathepsin O and was identical to the value reported for cathepsin L. At pH values higher than pH 6.0 cathepsin O was rapidly inactivated (FIG. 6) and an exact determination of pK2 is not possible.

Inhibitor profile of recombinant human cathepsin O

The efficacy of protease class specific inhibitors to inhibit cathepsin O was determined by adding the inhibitor to the purified enzyme in a fluorimetric enzyme assay (described above).

| INHIBITOR PROFILE FOR HUMAN CATHEPSIN O | | | |
|---|---|---|---|
| | | [I] | % inhibition |
| serine protease inhibitors | PMSF | 1 mM | 0 |
| | Befablock | 1 mM | 0 |
| | DIC | 1 mM | 0 |
| serine/cysteine protease inhibitors | leupeptin | 0.05 µM | 100 |
| | antipain | 0.05 µM | 100 |
| | elastatinal | 10 µM | 13 |
| | cymostatin | 0.1 µM | 100 |
| metallo-protease inhibitors | pepstatin | 10 µM | 0 |
| cysteine protease inhibitors | N-ethylmaleimide | 1 mM | 100 |
| | iodacetic acid | 50 µM | 80 |
| | cystatin | 0.1 µM | 100 |
| | E-64 | 0.1 µM | 100 |

Cathepsin O activity is only inhibited by cysteine protease specific inhibitors.

Substrate Specificity of recombinant human cathepsin O

The substrate specificity towards synthetic substrates was determined using the above described substrate assay. For the calculation of the kinetic parameters $k_{cat}$ and $K_m$ the initial rates were obtained typically at 9–11 different substrate concentrations, and the results are fitted to equation (1). The enzyme concentration is determined by active site titration with E-64 (Kindre et al., Biochem. J. 201: 367–372 (1982)).

$$v = \frac{kcat \times E0 \times [S]}{(Km + [S])} \quad \text{equation (1)}$$

The substrate specificity of human cathepsin O was similar to that of cathepsin L. The most important binding site in cysteine proteases of the papain superfamily is the S2 subsite pocket. When comparing the S2P2 specificity of the cathepsin O, L, S and B the similarities between the cathepsin O and L are obvious (FIG. 7). Both enzymes prefer larger hydrophobic residues in P2 of their substrates.

| Substrate Specificity (synthetic substrates) | | | |
|---|---|---|---|
| Substrate* | $k_{cat}(s^{-1})$ | $K_m(\mu M)$ | $k_{cat}/K_m(M^{-1}s^{-1})$ |
| Z-FR-MCA | 11.4 | 8.9 | 1,280,900 |
| Z-LR-MCA | 10.8 | 13.7 | 788,000 |
| Z-VR-MCA | 13.1 | 34.1 | 384,000 |
| Z-RR-MCA | 0.9 | 219 | 4,200 |
| Z-VVR-MCA | 2.8 | 14.6 | 192,000 |
| Z-LLR-MCA | 3.2 | 1 | 3,333,000 |
| Z-FVR-MCA | 0.3 | 4 | 65,000 |
| Z-VVVR-MCA | 0.2 | 6.5 | 29,000 |
| Suc-AAF-MCA (chymotrypsin substrate) | 0.2 | 6.5 | not hydrolyzed |
| Z-AAPR-MCA (trypsin substrate) | | | not hydrolyzed |
| MeOSuc-AAPV-MCA (HLE substrate) | | | not hydrolyzed |
| R-MCA (cathepsin H substrate) | | | not hydrolyzed |

*in 100 mM acetate buffer, pH 5.5 containing 2.5 mM DTT/EDTA

Activities of recombinant human cathepsin O towards extracellular matrix proteins At pH 5.5, cathepsin O displayed an elastinolytic activity towards insoluble porcine elastin comparable to cathepsin L and bovine elastase, but only 50% of the appropriate human cathepsin S activity towards elastin. However, cathepsin was inactivated at prolonged times faster than the other proteases. At neutral pH both cathepsin O and L are essentially inactive.

The collagenolytic activity of human cathepsin O is high and comparable to cathepsin L (FIG. 7).

The ability of cathepsin O to degrade extracellular matrix proteins such as elastin and collagen emphasize its potential function in tissue and especially in bone remodelling. Recombinant human cathepsin O may be useful in the treatment of the discus hernia as a replacement of the still recently used plant cysteine protease chymopapain.

| Relative elastinolytic activities of cathepsins compared with the bovine pancreatic elastase | | | |
|---|---|---|---|
| Protease | pH 4.5 mg/min/µmol enzyme | pH 5.5 mg/min/µmol enzyme | pH 7.0 mg/min/µmol enzyme |
| cathepsin O | 41 | 16 | 0 |
| cathepsin L | 18 | 32 | 0 |
| cathepsin S | 146 | 102 | 55 |
| pancreatic elastase | 8 | 18 | 79 |

Tissue distribution of human cathepsin O on the message level

The tissue distribution of the message level of human cathepsins O, L and S was determined by Northern blotting using cDNA probes of the appropriate human enzymes. The probes were approximately 450 base pairs long and stretched over the region coding for the residues between the active site residues cysteine-25 (according to the papain numbering) and asparagine-175. FIG. 8 shows Northern blots for human cathepsin O.

The tissue distribution of human cathepsin O mRNA showed some similarities to cathepsin L, however, its tissue concentration seemed significantly lower in most of the organs (heart, placenta, lung, pancreas and kidney). On the other hand human cathepsin O displayed remarkable differences in its distribution in human tissues and cell lines when compared with the human cathepsins L and S. Cathepsin O showed high levels of transcription in ovary, small intestine and colon but no message in liver, which is rich for cathepsin L. It was also found in HeLa cells.

| Tissue and cell line distribution (Northern Blotting) | | | |
|---|---|---|---|
| Tissue | HCATO | HCATL | HCATS |
| heart | xx | xxxx | — |
| brain | — | x | — |
| placenta | xx | xxxx | xx |
| lung | xx | xxx | xxx |
| liver | — | xxxx | xx |
| skeletal muscle | xx | xx | — |
| kidney | x | xxxx | — |
| pancreas | x | xx | — |
| spleen | x | — | x |
| thymus | x | x | — |
| prostate | x | x | — |
| testis | x | xx | — |
| ovary | xxx | x | — |
| small intestine | xx | — | — |
| colon | xxx | x | — |
| leukocytes | — | — | xxx |
| promyelocyt.leukemia HL-60 | — | — | x |
| HeLa S3 | xx | x | x |
| lymphoblast.leukemia MOLT-4 | — | xx | x |

-continued

| Tissue and cell line distribution (Northern Blotting) | | | |
|---|---|---|---|
| Tissue | HCATO | HCATL | HCATS |
| Burkitt's lymphoma Raji | — | — | x |
| colect.adenocarcinoma | — | x | — |
| lung carcinoma A549 | — | xxxx | x |
| melanoma G361 | — | xxxxx | — |

We claim:

1. A recombinant nucleic acid consisting of a nucleic acid encoding amino acids −99 to −1 as set forth in FIG. 1 (amino acids 16–114 of SEQ ID NO:2).

2. An expression vector comprising transcriptional and translational regulatory DNA operably linked to nucleic acid according to claim 1.

3. A host cell transformed with an expression vector according to claim 2.

4. A method of producing the propart of cathepsin O protein comprising:

a) culturing a host cell transformed with an expression vector according to claim 2; and b) expressing said nucleic acid to produce said propart of cathepsin O protein.

5. A host cell transformed with nucleic acid according to claim 1.

6. A method of producing the propart of cathepsin O protein comprising:

a) culturing a host cell transformed with nucleic acid according to claim 1; and b) expressing said nucleic acid to produce said propart of cathepsin O protein.

\* \* \* \* \*